United States Patent
Kurokawa

(10) Patent No.: US 10,416,266 B2
(45) Date of Patent: Sep. 17, 2019

(54) MAGNETIC RESONANCE IMAGING APPARATUS AND METHOD FOR REDUCING UNNECESSARY CONTRAST

(71) Applicant: HITACHI, LTD., Tokyo (JP)

(72) Inventor: Shinji Kurokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1066 days.

(21) Appl. No.: 14/762,271

(22) PCT Filed: Feb. 13, 2014

(86) PCT No.: PCT/JP2014/053283
§ 371 (c)(1),
(2) Date: Jul. 21, 2015

(87) PCT Pub. No.: WO2014/126134
PCT Pub. Date: Aug. 21, 2014

(65) Prior Publication Data
US 2015/0355304 A1 Dec. 10, 2015

(30) Foreign Application Priority Data
Feb. 15, 2013 (JP) ................................ 2013-027918

(51) Int. Cl.
*G01R 33/561* (2006.01)
*A61B 5/055* (2006.01)
(Continued)

(52) U.S. Cl.
CPC .......... *G01R 33/5617* (2013.01); *A61B 5/055* (2013.01); *G01R 33/36* (2013.01);
(Continued)

(58) Field of Classification Search
USPC .......................... 324/300–322; 600/407–435; 382/128–131
See application file for complete search history.

(56) References Cited

U.S. PATENT DOCUMENTS

| 5,239,266 A | 8/1993 | Kaufman et al. |
| 6,054,853 A | 4/2000 | Miyamoto et al. |
(Continued)

FOREIGN PATENT DOCUMENTS

| JP | H6-277197 | 10/1994 |
| JP | H11-128200 | 5/1999 |
(Continued)

*Primary Examiner* — Melissa J Koval
*Assistant Examiner* — Tiffany A Fetzner
(74) *Attorney, Agent, or Firm* — Cooper & Dunham LLP

(57) ABSTRACT

In multi-echo imaging, in imaging in which pulses other than a 180° pulse are included in refocus RF pulses, a high-quality image in which the intended contrast is emphasized is obtained by reducing unnecessary contrast. Therefore, imaging parameters are adjusted so as to reduce the unnecessary contrast. The adjustment is performed so that, for echo signals from tissues having the same relaxation time to cause intended contrast among echo signals from a plurality of tissues having different relaxation times, the difference between the signal strengths of echo signals to determine the contrast, such as echo signals at the k-space center, is reduced. Imaging parameters to be adjusted include a repetition time, the FA of a DE pulse, the FA of a saturation pulse, the application timing of the saturation pulse, the application strength of a gradient magnetic field in a recovery period, application timing, and the like.

19 Claims, 20 Drawing Sheets

(51) Int. Cl.
  *G01R 33/56* (2006.01)
  *G01R 33/54* (2006.01)
  *G01R 33/48* (2006.01)
  *G01R 33/385* (2006.01)
  *G01R 33/36* (2006.01)

(52) U.S. Cl.
  CPC ....... *G01R 33/385* (2013.01); *G01R 33/4818* (2013.01); *G01R 33/543* (2013.01); *G01R 33/5602* (2013.01); *G01R 33/546* (2013.01)

(56) References Cited

U.S. PATENT DOCUMENTS

| | | | | |
|---|---|---|---|---|
| 6,219,571 | B1* | 4/2001 | Hargreaves | A61B 5/055 324/307 |
| 8,664,954 | B2* | 3/2014 | Hetzer | G01R 33/4818 324/309 |
| 9,041,393 | B2* | 5/2015 | Warntjes | G01R 33/5602 324/307 |
| 9,494,668 | B2* | 11/2016 | Bottomley | G01R 33/54 |
| 2003/0042905 | A1 | 3/2003 | Miyazaki et al. | |
| 2005/0001617 | A1 | 1/2005 | Busse | |
| 2008/0161678 | A1 | 7/2008 | Miyazaki et al. | |
| 2011/0018537 | A1* | 1/2011 | Warntjes | G01R 33/5602 324/309 |
| 2012/0013336 | A1* | 1/2012 | Hetzer | G01R 33/4818 324/309 |
| 2013/0141096 | A1* | 6/2013 | Bottomley | G01R 33/50 324/309 |
| 2014/0077805 | A1 | 3/2014 | Hoshino et al. | |
| 2015/0355304 | A1* | 12/2015 | Kurokawa | A61B 5/055 324/309 |

FOREIGN PATENT DOCUMENTS

| | | |
|---|---|---|
| JP | 2003-70766 | 3/2003 |
| JP | 2003-305020 | 10/2003 |
| JP | 2005-21690 | 1/2005 |
| JP | 2007-313303 | 12/2007 |
| WO | WO2012/169350 A1 | 12/2012 |

* cited by examiner

FIG.5
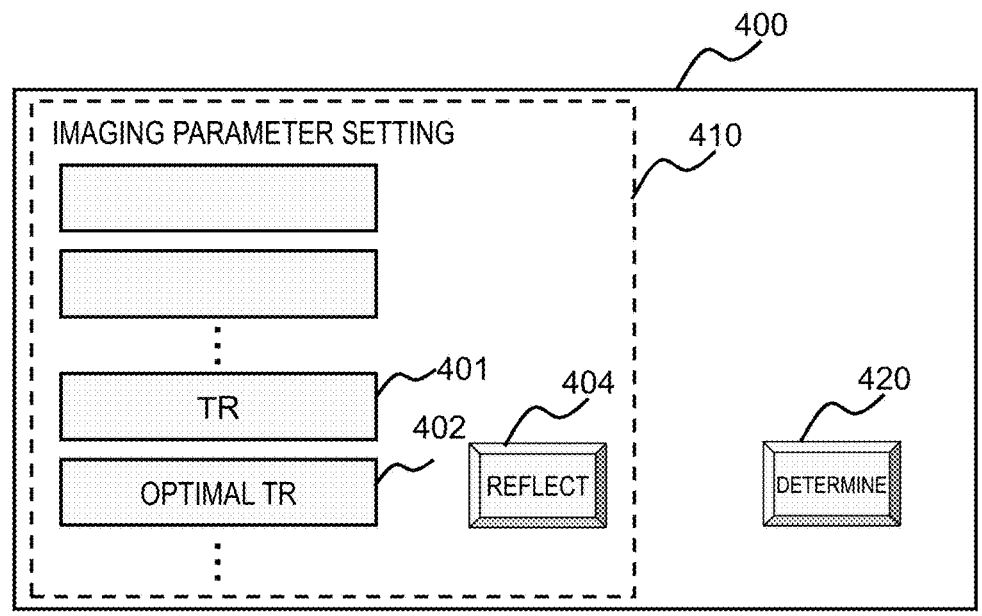
(a)
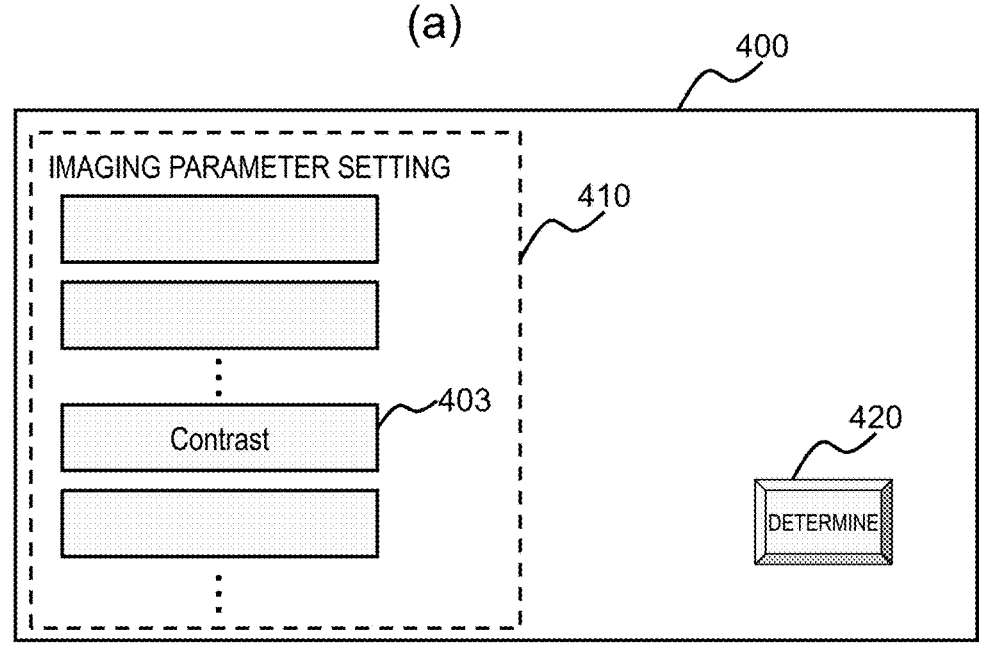
(b)

FIG.7
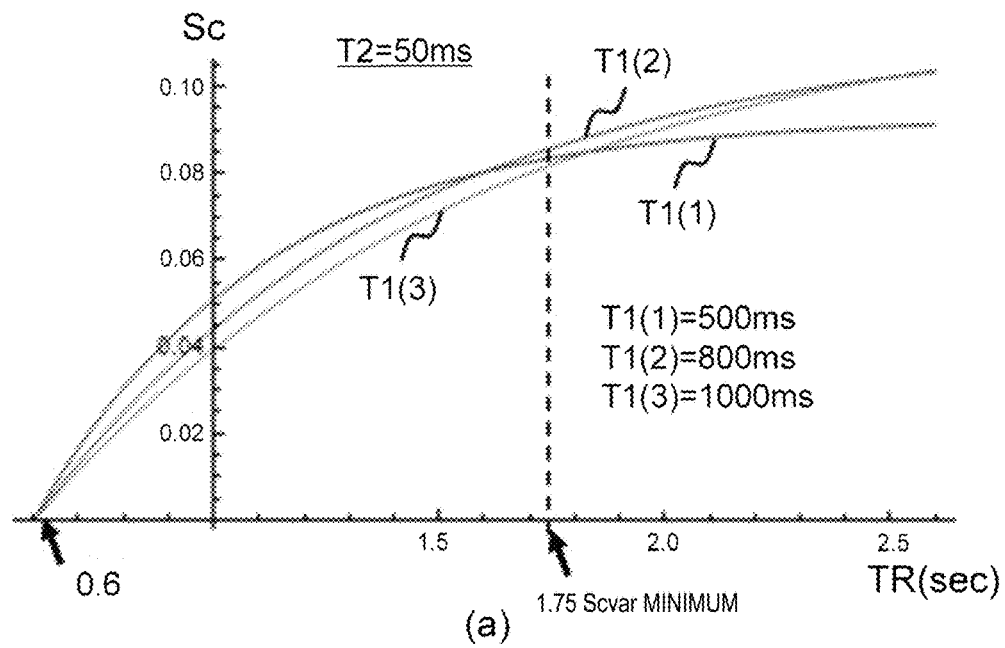
(a)
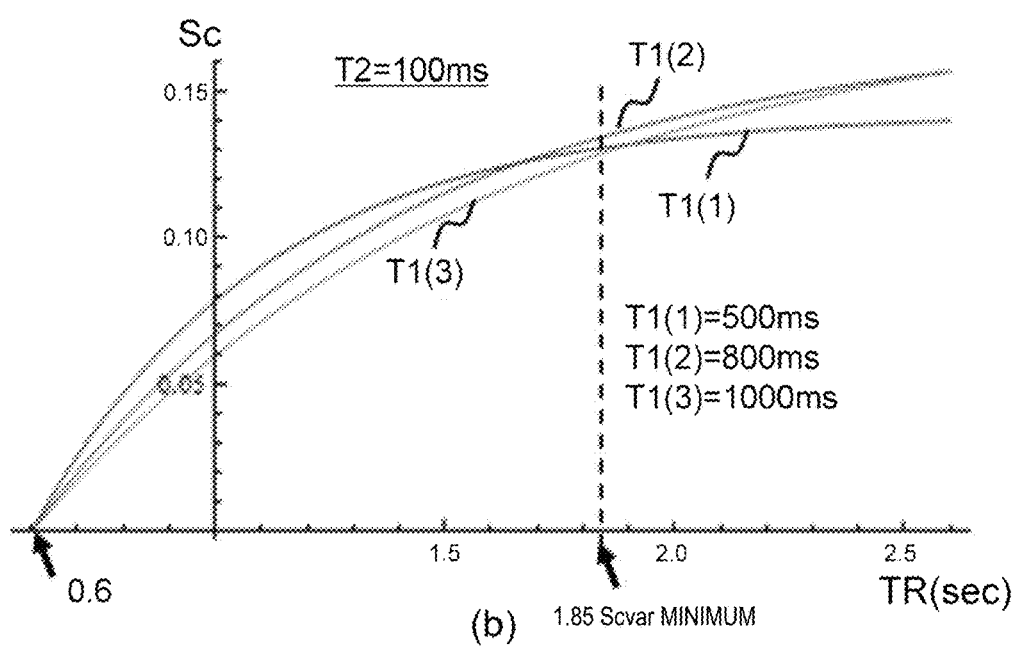
(b)

FIG.17
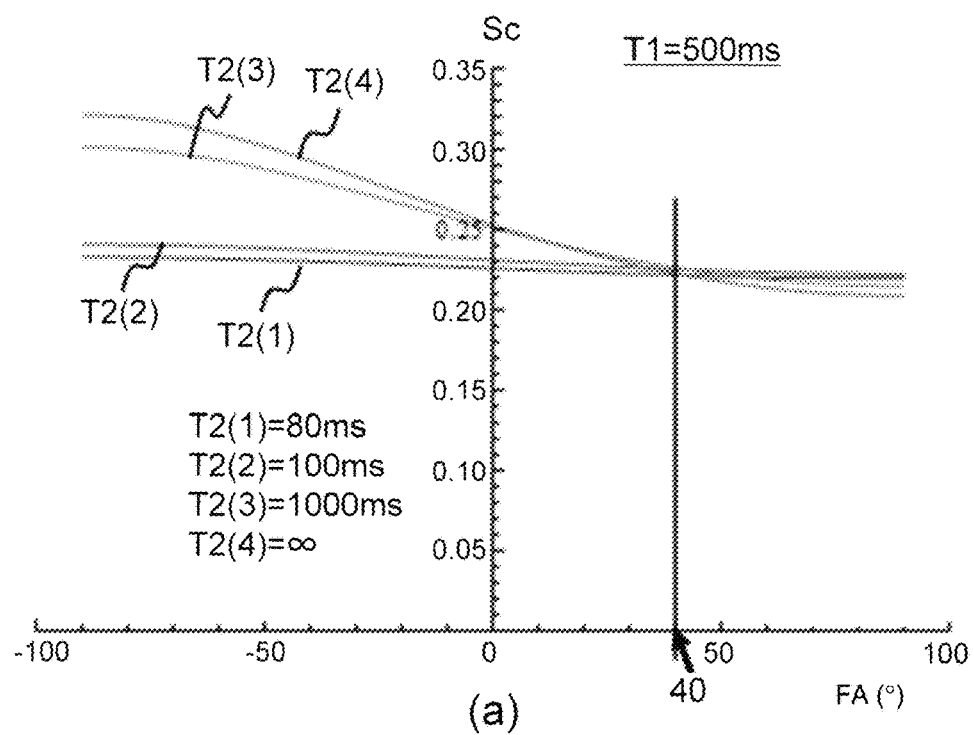
(a)
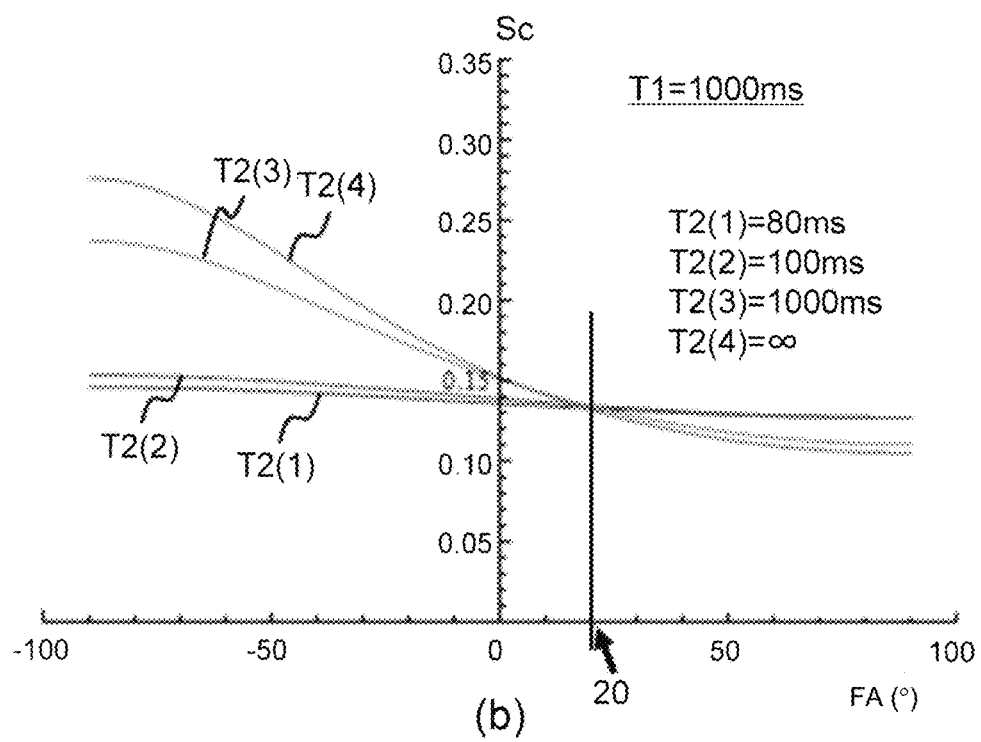
(b)

MAGNETIC RESONANCE IMAGING APPARATUS AND METHOD FOR REDUCING UNNECESSARY CONTRAST

TECHNICAL FIELD

The present invention relates to a nuclear magnetic resonance imaging (hereinafter, referred to as "MRI") technique of measuring a nuclear magnetic resonance (hereinafter, referred to as "NMR") signal from hydrogen, phosphor, or the like in an object and imaging nuclear density distribution, relaxation time distribution, or the like, and in particular, to a technique of adjusting the contrast of an image.

BACKGROUND ART

The MRI apparatus is an apparatus that measures an NMR signal generated by the object, especially, the spins of nuclei which form human tissue, and images the shapes or functions of the head, abdomen, limbs, and the like in a two-dimensional manner or in a three-dimensional manner. In the imaging, NMR signals are subjected to different phase encoding by the gradient magnetic field and subjected to frequency encoding, and are measured as time-series data. The measured NMR signals are reconstructed as an image by a two-dimensional or three-dimensional Fourier transform.

As one of the imaging methods, there is fast spin eo (FSE). The FSE is an imaging method for reducing the imaging time by acquiring a plurality of echoes (echo trains) by applying a plurality of refocus RF pulses (180° pulses) for one excitation RF pulse (90° pulse). Such an imaging method is referred to as multi-echo imaging. In the echo train, transverse magnetization is attenuated in transverse relaxation time T2 (T2 attenuation). Accordingly, if the echo train is too long, the signal strength may be insufficient in the echo near the end.

As a method for solving this, there is a method called variable refocus flip angle (VRFA) to change the flip angle (FA) of a refocus RF pulse. In the VRFA, the signal strength is prolonged by making the components of the longitudinal magnetization be included in the echo signal by changing the FA appropriately. In addition, the longitudinal magnetization is recovered in the longitudinal relaxation time T1, but is attenuated in the T1 when components contributing to the generation of the echo signal in the echo train are taken into consideration. In this specification, this is referred to as T1 attenuation. In many tissues, T1 is sufficiently longer than T2. Therefore, in the VRFA, attenuation in the echo train can be delayed by making the components of the longitudinal magnetization be included.

Since the relaxation times T1 and T2 are tissue-specific characteristics, the relaxation times T1 and T2 are determined by the tissue. There are T1-weighted (T1W) imaging for imaging a difference (T1 contrast) in the relaxation time T1 between two different tissues using this and T2-weighted (T2W) imaging for imaging a difference (T2 contrast) in the relaxation time T2 between two different tissues using this. When acquiring the T1-weighted image, the maximization of the T1 contrast and the reduction of the T2 contrast are important. In addition, when acquiring the T2-weighted image, maximization of the T2 contrast and reduction of the T1 contrast are important. Generally, in the SE sequence including the FSE, the influence due to the difference in the relaxation time T1 (influence due to T1 attenuation; T1 contrast) can be reduced by setting the TR (repetition period) to be long, and the influence due to the difference in the relaxation time T2 (influence due to T2 attenuation; T2 contrast) can be reduced by setting the TE (echo time) to be short. The TR does not affect the T2 contrast, and the TE does not affect the T1 contrast.

However, in the VRFA, since the components of the longitudinal magnetization are also included in the echo signal, a change in the signal strength within the echo train is based on both the T1 attenuation and the T2 attenuation. That is, both the influence of the T1 attenuation and the influence of the T2 attenuation are mixed. Therefore, in the VRFA, the TE affects both of the T1 contrast and the T2 contrast. The VRFA is a technique for making the echo train as long as possible. However, if the echo train is too long, T2 attenuation in the echo train affects the T2 contrast. Accordingly, the length of the echo train is also limited in this respect.

In such a VRFA, in order to maximize the T1 contrast when acquiring the T1-weighted image, there is a method of reversing the magnetization in the last part of the echo train (for example, refer to PTL 1). In this method, since the signal difference is maximized at the head of the echo train, reversal of the contrast due to the T2 attenuation in the echo train is unlikely to occur. Accordingly, the T1 contrast is maintained over the entire echo train.

CITATION LIST

Patent Literature

[PTL 1] U.S. Pat. No. 7,639,010

SUMMARY OF INVENTION

Technical Problem

However, in the technique disclosed in PTL 1, only the T1 contrast is increased or the influence of T2 is also used to create a contrast close to the T1 contrast, but reducing the T2 contrast in T1-weighted imaging has not been taken into consideration. Therefore, in the technique disclosed in PTL 1, it is thought that it is difficult to obtain the normal T1 contrast for various tissues.

As a second problem, there is a mixing of the T1 contrast in the T2-weighted imaging. Since the relaxation time T1 is longer than the transverse relaxation time T2, a contrast change due to the influence of T1 attenuation is not generally important in the T2-weighted imaging. However, in practice, this change cannot be neglected.

When the time constants T1 and T2 are known, even if the T1 attenuation and the T2 attenuation are mixed, it is possible to adjust the FA of the refocus RF pulse so that the conventional T2 contrast is obtained. However, these time constants T1 and T2 differ depending on the tissue to be imaged. For this reason, it is difficult to perform adjustment in consideration of an infinite number of combinations of the time constants T1 and T2. For example, adjustment for the normal tissue may not be effective in imaging using a contrast agent.

Thus, as in the VRFA, when an RF pulse having the FA that is not 180° is applied as a refocus RF pulse, the maximization of the T1 contrast and the reduction of the T2 contrast are required in order to obtain the satisfactory T1 contrast when capturing the T1-weighted image. In addition, in order to obtain the satisfactory T2 contrast when capturing the T2W image, the reduction of the T1 contrast and the maximization of the T2 contrast are required. However, under the present circumstances, it is not possible to realize these.

The present invention has been made in view of the above situation, and it is an object of the present invention to obtain a high-quality image, in which the intended contrast is emphasized, by reducing unnecessary contrast, in imaging in which pulses other than a 180° pulse are included in refocus RF pulses, in multi-echo imaging.

Solution to Problem

In the present invention, an imaging parameter is adjusted so as to reduce the unnecessary contrast. The adjustment is performed so that, for echo signals from tissues having the same relaxation time to cause intended contrast among echo signals from a plurality of tissues having different relaxation times, the difference between the signal strengths of echo signals to determine the contrast, such as echo signals at the k-space center, is reduced.

Imaging parameters to be adjusted include a repetition time, the FA of a DE pulse, the FA of a saturation pulse, the application timing of the saturation pulse, the application strength of a gradient magnetic field in a recovery period, application timing, and the like.

In addition, the imaging parameters after the adjustment to reduce the influence of T1 attenuation or T2 attenuation are presented to the user, so that the user can refer to them for contrast adjustment.

Advantageous Effects of Invention

According to the present invention, it is possible to obtain a high-quality image, in which the intended contrast is emphasized, by reducing unnecessary contrast, in imaging affected by both of T1 relaxation and T2 attenuation in multi-echo imaging.

BRIEF DESCRIPTION OF DRAWINGS

FIGS. 5(a) and 5(b) are diagrams for explaining an imaging parameter input screen in the first embodiment.

FIGS. 7(a) and 7(b) are diagrams for explaining a specific example of parameter adjustment.

FIGS. 17(a) and 17(b) are diagrams for explaining the adjustment process in the second embodiment.

DESCRIPTION OF EMBODIMENTS

<<First Embodiment>>

Figure 1:
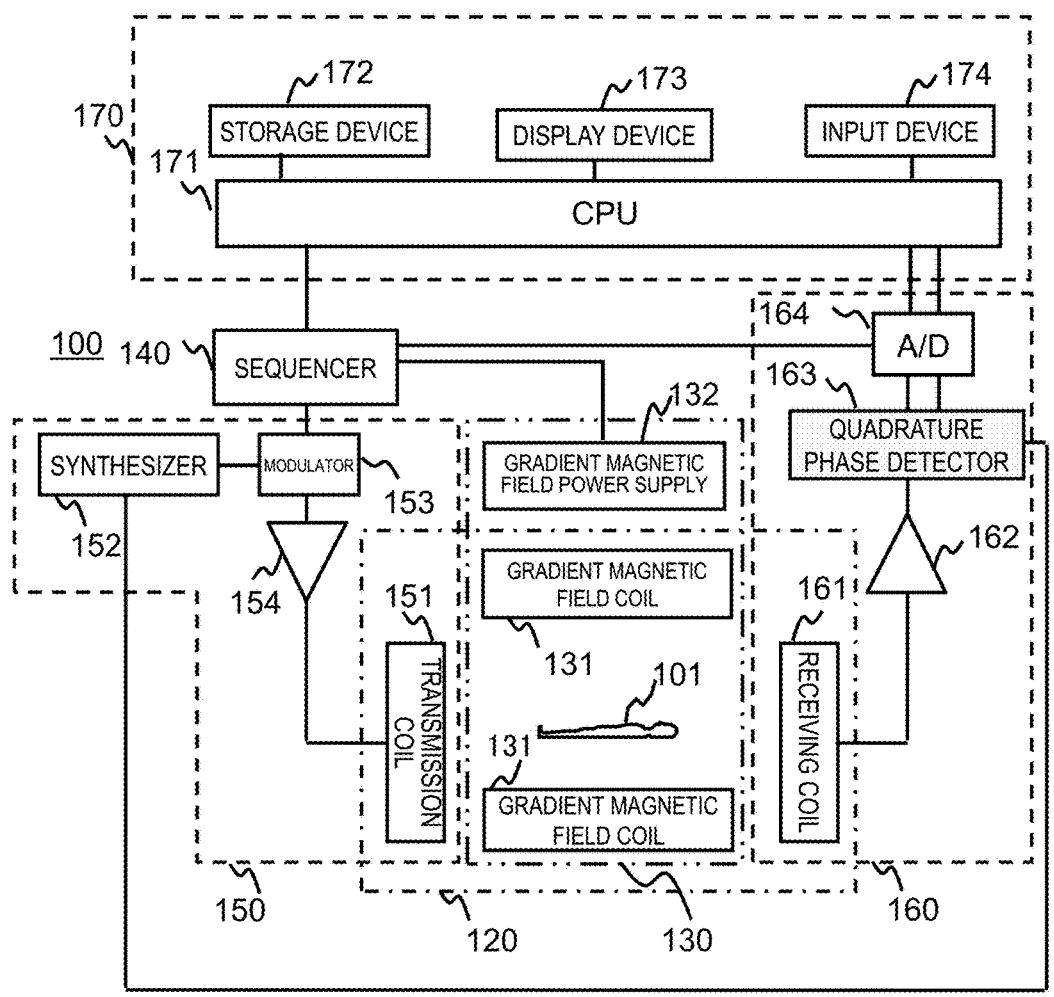
FIG. 1 is a block diagram of an MRI apparatus of a first embodiment.

Hereinafter, a first embodiment to which the present invention is applied will be described. Hereinafter, in all diagrams for explaining the embodiments of the present invention, the same reference numerals are given to components having the same functions, and repeated explanation thereof will be omitted.

First, the overview of an example of an MRI apparatus 100 of the present embodiment will be described with reference to FIG. 1. FIG. 1 is a block diagram showing the overall configuration of the MRI apparatus 100 of the present embodiment. The MRI apparatus 100 of the present embodiment obtains a tomographic image of an object 101 using the NMR phenomenon. As shown in FIG. 1, the MRI apparatus 100 includes a static magnetic field generation unit 120 that generates a static magnetic field, a gradient magnetic field generation unit 130 that applies a gradient magnetic field to the object 101 placed in the static magnetic field, a signal transmission unit 150 that transmits a high-frequency magnetic field pulse to excite the magnetization of the object 101 at a predetermined flip angle, a signal receiving unit 160 that receives an echo signal generated by the object 101, a control unit 170 that reconstructs an image from the echo signal received by the signal receiving unit 160 and that controls the operations of the gradient magnetic field generation unit 130, the signal transmission unit 150, and the signal receiving unit 160 according to the imaging sequence, and a sequencer 140.

The static magnetic field generation unit 120 generates a uniform static magnetic field in the space around the object 101 in a direction perpendicular to the body axis in the case of a vertical magnetic field method and in the body axis direction in the case of a horizontal magnetic field method, and includes a permanent magnet type, normal conduction type, or superconducting type static magnetic field generator disposed around the object 101.

The gradient magnetic field generation unit 130 includes gradient magnetic field coils 131 wound in three axial directions of X, Y, and Z, which are the coordinate system (device coordinate system) of the MRI apparatus 100, and a gradient magnetic field power supply 132 that drives each gradient magnetic field coil, and applies gradient magnetic field pulses Gx, Gy, and Gz in the three axial directions of X, Y, and Z by driving the gradient magnetic field power supply 132 of each gradient magnetic field coil 131 according to a command from the sequencer 140 to be described later. The gradient magnetic field pulses Gx, Gy, and Gz are applied in a direction perpendicular to the slice plane (imaging section) at the time of imaging in order to set a slice plane for the object 101, and are applied in two remaining directions, which are perpendicular to the set slice plane and are perpendicular to each other, in order to encode position information in the two directions in the NMR signal (echo signal). The gradient magnetic field pulse applied in order to set the slice plane is referred to as a slice direction gradient magnetic field pulse (Gs), and the gradient magnetic field pulses applied in the other two directions are referred to as a phase encoding direction gradient magnetic field pulse (Gp) and a frequency encoding direction gradient magnetic field pulse (Gf), respectively.

The signal transmission system 150 emits a high-frequency magnetic field pulse (hereinafter, referred to as an "RF pulse") to the object 101 in order to cause nuclear magnetic resonance in the nuclear spins of atoms that form the body tissue of the object 101, and includes a high frequency oscillator (synthesizer) 152, a modulator 153, a high frequency amplifier 154, and a high frequency coil (transmission coil) 151 on the transmission side. The high frequency oscillator 152 generates an RF pulse, and outputs the RF pulse at the timing according to the command from the sequencer 140. The modulator 153 performs amplitude modulation of the output RF pulse, and the high frequency amplifier 154 amplifies the amplitude-modulated RF pulse and supplies it to the transmission coil 151 disposed near the object 101. The transmission coil 151 emits the supplied RF pulse to the object 101.

The signal receiving unit 160 detects a magnetic resonance signal (an echo signal, an NMR signal) emitted by the nuclear magnetic resonance of the nuclear spins, which form the body tissue of the object 101, and includes a high frequency coil (receiving coil) 161 on the receiving side, a signal amplifier 162, a quadrature phase detector 163, and an A/D converter 164. The receiving coil 161 is disposed near the object 101, and detects an NMR signal of the response from the object 101 that is induced by the electromagnetic wave emitted from the transmission coil 151. The detected NMR signal is amplified by the signal amplifier 162 and is then divided into two orthogonal signals by the quadrature phase detector 163 at the timing according to the command from the sequencer 140. Each of the orthogonal signals is converted into the digital amount by the A/D converter 164 and is transmitted to the control unit 170.

The sequencer 140 applies an RF pulse and a gradient magnetic field pulse repeatedly according to a predetermined pulse sequence. The pulse sequence describes the timing or the strength of a high-frequency magnetic field, a gradient magnetic field, and signal reception, and is stored in advance in the control unit 170. The sequencer 140 operates according to the instruction from the control unit 170, and transmits various commands, which are required for data collection of a tomographic image of the object 101, to the signal transmission unit 150, the gradient magnetic field generation unit 130, and the signal receiving unit 160.

The control unit 170 performs overall control of the MRI apparatus 100, various operations such as data processing, display and storage of processing results, and the like, and includes a CPU 171, a storage device 172, a display device 173, and an input device 174. The storage device 172 is formed by an internal storage device, such as a hard disk, and an external storage device, such as an external hard disk, an optical disc, and a magnetic disk. The display device 173 is a CRT, a liquid crystal display device, or the like. The input device 174 is an interface for inputting various kinds of control information of the MRI apparatus 100 or control information of processing performed in the control unit 170. For example, the input device 74 includes a trackball, a mouse, and a keyboard. The input device 174 is disposed near the display device 173. The operator inputs instructions and data, which are required for various kinds of processing of the MRI apparatus 100, interactively through the input device 174 while observing the display device 173.

The CPU 171 realizes the control of the operation of each unit of the MRI apparatus 100 and each process of the control unit 170, such as various kinds of data processing, by executing a program stored in advance in the storage device 172 according to the instruction input by the operator. For example, when the data from the signal receiving unit 160 is input to the control unit 170, the CPU 171 executes processing, such as signal processing and image reconstruction, and displays a tomographic image of the object 101, which is the result, on the display device 173 and records the tomographic image of the object 101 in the storage device 172.

The transmission coil 151 and the gradient magnetic field coil 131 are provided in the static magnetic field space of the static magnetic field generation unit 120, into which the object 101 is inserted, so as to face the object 101 in the case of a vertical magnetic field method and so as to surround the object 101 in the case of a horizontal magnetic field method. In addition, the receiving coil 161 is provided so as to face or surround the object 101.

Currently, nuclides imaged by the MRI apparatus, which are widely used clinically, are a hydrogen nucleus (proton) that is a main constituent material of the object 101. In the MRI apparatus 100, the shapes or functions of the head, abdomen, limbs, and the like of the human body are imaged in a two-dimensional or in a three-dimensional manner by imaging the information regarding the spatial distribution of the proton density or the spatial distribution of the relaxation time of the excitation state.

The imaging sequence by which the CPU 171 of the control unit 170 applies a control signal to the sequencer 140 is determined by a pulse sequence, by which the application timing of the RF pulse and the gradient magnetic field pulse is determined, and imaging parameters that specify the application strength, application timing, and the like of the RF pulse and the gradient magnetic field pulse. The pulse sequence is set in advance, and is stored in the storage device 172.

Figure 2:
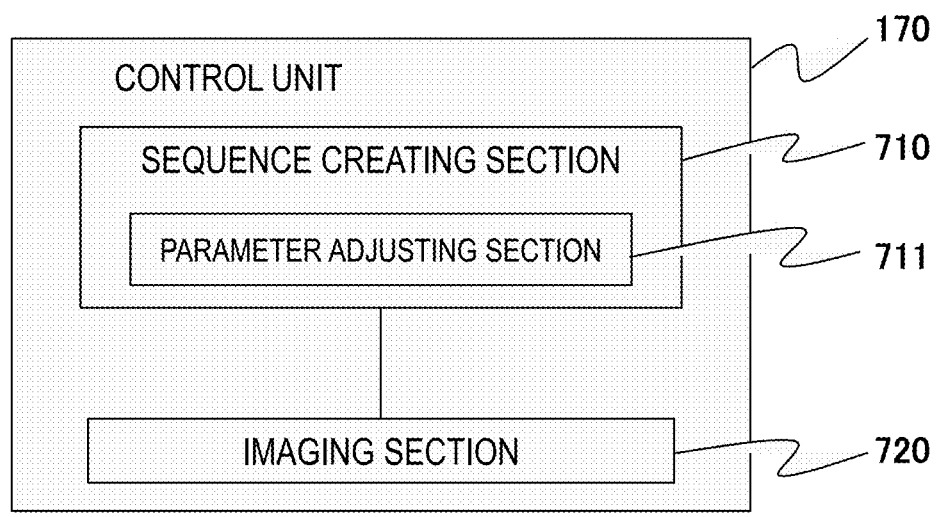
FIG. 2 is a functional block diagram of a control unit of the first embodiment.

As shown in FIG. 2, the control unit 170 of the present embodiment includes a sequence creating section 710 that receives imaging parameters from the user and creates an imaging sequence used in the imaging using the imaging parameters and a pulse sequence stored in advance and an imaging section 720 that performs imaging by controlling each unit according to the created imaging sequence. The sequence creating section 710 is realized when the CPU 171 loads a program stored in advance in the storage device 172 to the memory and executes the program.

Prior to detailed explanation of the sequence creating section 710 of the present embodiment, the above pulse sequence example used in the present embodiment will be described. In the present embodiment, a pulse sequence for multi-echo imaging, such as FSE, is used as the pulse sequence. Hereinafter, in the present embodiment, a case of using the FSE pulse sequence will be described as an example.

Figure 3:
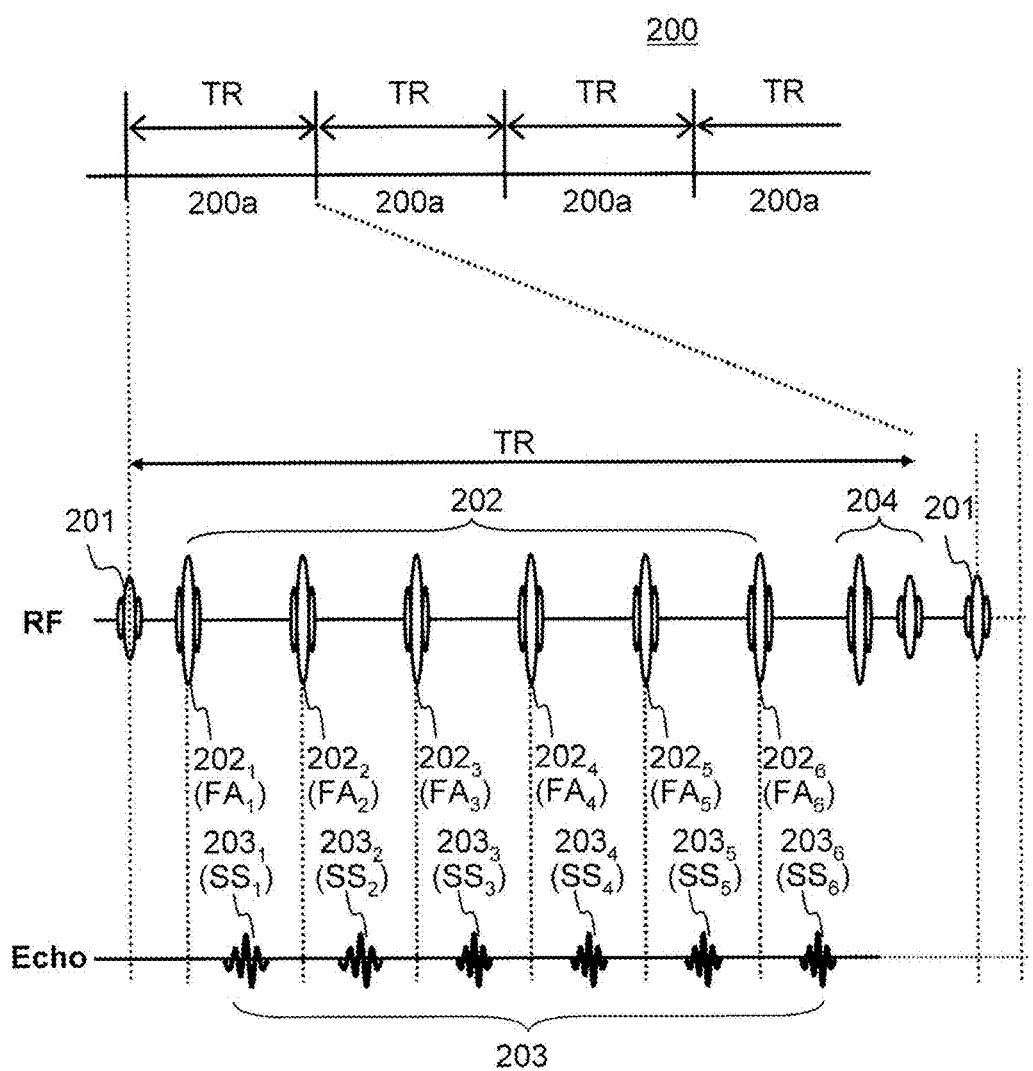
FIG. 3 is a pulse sequence diagram of the FSE sequence in the first embodiment.

FIG. 3 shows the application timing of an RF pulse of an FSE pulse sequence 200 and the acquisition timing of an echo signal. As shown in this diagram, in the FSE pulse sequence 200, the execution of a sequence 200a within the repetition time TR is repeated every TR.

In the sequence 200a within the TR, a refocus RF pulse 202 is applied N (N is a natural number) times after one excitation RF pulse 201. Each refocus RF pulse 202 applied is expressed as a refocus RF pulse $202_n$ (n is a natural number satisfying $1 \leq n \leq N$). The subscript n is given in order of application. The flip angle of the refocus RF pulse $202_n$ applied for the n-th time is expressed as $FA_R$. The flip angle $FA_n$ of the refocus RF pulse $202_n$ applied for the n-th time is referred to as the n-th FA. An echo signal $203_n$ is measured immediately after the refocus RF pulse $202_n$ applied for the n-th time, and the echo number is set to n. The signal strength SS of each echo signal $203_n$ is expressed as $SS_n$. In the signal strength SS used herein, a strength change due to various kinds of encoding is neglected.

These are referred to as the refocus RF pulse 202, the flip angle FA, the echo signal 203, and the signal strength SS, respectively, when it is not necessary to distinguish these from each other in particular. FIG. 3 illustrates a case of applying the six refocus RF pulses 202 as an example.

In the present embodiment, a driven equilibrium pulse (DE pulse) 204 is applied after echo train acquisition. The DE pulse 204 is a pulse to return the transverse magnetization remaining after the echo train to the longitudinal magnetization. By the application of the DE pulse 204, it is possible to shorten the waiting time until the longitudinal magnetization is recovered.

In the present embodiment, among the FSE pulse sequences 200, a VRFA sequence 200 in which each flip angle $FA_n$ of the refocus RF pulse 202 is variable is used as a pulse sequence.

Figure 4:
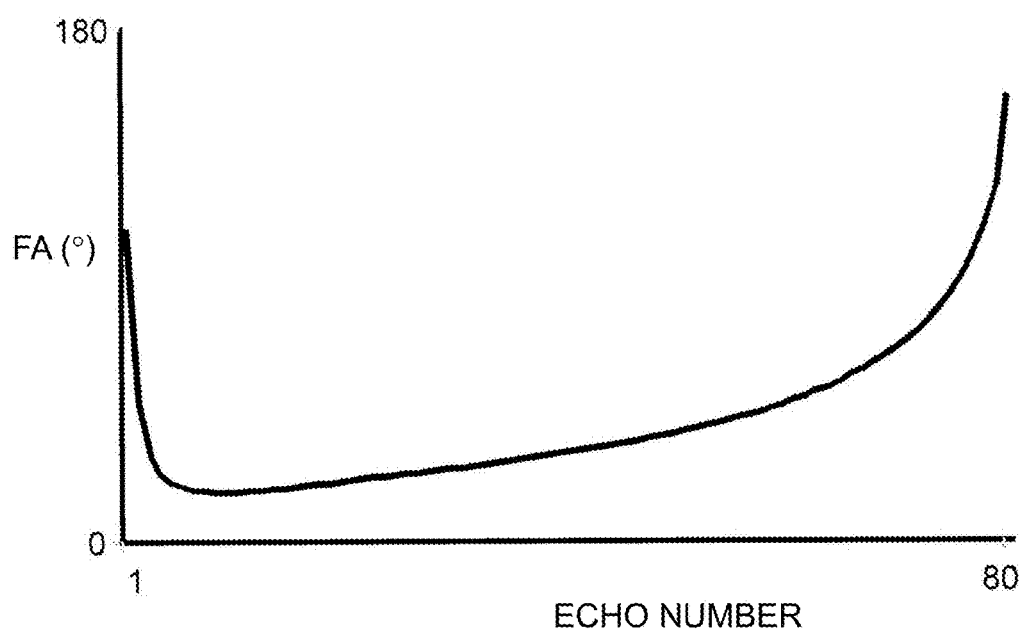
FIG. 4 is a diagram for explaining an example of the FA change shape in the first embodiment.

In this case, a sequential arrangement (FA value column) of the values of the flip angles $FA_n$ of the first to N-th refocus RF pulses $202_n$ is referred to as an FA change shape FAP, and a sequential arrangement of the signal strength $SS_n$ of the first to N-th echo signals $203_n$ is referred to as a signal strength change shape SSP. That is, the FA change shape FAP is configured to include the flip angle FA of each refocus RF pulse 202, and the signal strength change shape SSP is configured to include the signal strength SS of each echo signal obtained for each refocus RF pulse 202. FIG. 4 shows an example of the FA change shape FAP.

The pulse sequence used in the present embodiment is not limited to the so-called VRFA sequence 200 in which the FA changes gradually. Any pulse sequence may be used in which an RF pulse having the FA other than 180° is included in the refocus RF pulses 202. For example, the FA of all of the refocus RF pulses 202 may be 150°.

In addition, the pulse sequence used in the present embodiment is not limited to the FSE pulse sequence 200 either. Any pulse sequence may be used in which a plurality of refocus RF pulses are applied within the repetition time TR after the application of the excitation RF pulse (90° pulse) and in which at least one flip angle of the refocus RF pulse is not 180°.

As described above, when the VRFA sequence 200 is used in the imaging, the flip angle FA of the refocus RF pulse 202 is variable, and a case in which the flip angle FA of the refocus RF pulse 202 is not 180° is included. For this reason, the longitudinal magnetization also changes with the application of the refocus RF pulse 202. Therefore, the influence of T1 attenuation (T1 contrast) and the influence of T2 attenuation (T2 contrast) are mixed.

In the present embodiment, when acquiring an image with a predetermined contrast, unnecessary contrast is reduced. In order to realize this, as shown in FIG. 2, the sequence creating section 710 of the present embodiment includes a parameter adjusting section 711 that adjusts an imaging parameter to be adjusted, which is set in advance, so as to reduce the unnecessary contrast.

The parameter adjusting section 711 of the present embodiment adjusts the imaging parameter to be adjusted so that the difference between the signal strengths of echo signals arranged at the k-space center, among echo signals from tissues having the same first relaxation time to cause the intended contrast and different second relaxation times to cause unnecessary contrast, is reduced.

Hereinafter, in the present embodiment, a case in which an image to be acquired is a T2 contrast image, that is, a T2-weighted image and the unnecessary contrast is T1 contrast will be described as an example. The parameter adjusting section 711 of the present embodiment adjusts an adjustment parameter using the signal strengths of echo signals arranged at the k-space center, among echo signals from a plurality of tissues having different combinations of T1 and T2. When T2 is the same, adjustment is performed so that the signal strength difference is reduced even if T1 is different.

That is, the parameter adjusting section 711 of the present embodiment adjusts a parameter to be adjusted, which is set in advance, so as to reduce the influence (T1 contrast) of T1 attenuation causing unnecessary contrast when acquiring the T2-weighted image. Hereinafter, the influence of T1 attenuation is also simply referred to as the influence of T1. In addition, the parameter to be adjusted is referred to as an adjustment parameter.

The imaging parameter used as an adjustment parameter is assumed to be at least one of a high-frequency magnetic field pulse and a gradient magnetic field that are applied during a recovery period from the application of the last refocus RF pulse 202 of the echo train to the application of the next excitation RF pulse 201. For example, the imaging parameter is the length of a recovery period from the end of the echo train to the next TR, an application parameter of an RF pulse applied during the recovery period, an application parameter of a gradient magnetic field applied during the recovery period, or the like. Examples of the RF pulse applied during the recovery period include the DE pulse 204, a saturation pulse to be described later, and the like. In addition, the application parameter to be adjusted of the DE pulse 204 and the saturation pulse is FA. In the case of the saturation pulse, the application timing is also an application parameter to be adjusted. Examples of the application parameter of the gradient magnetic field applied during the recovery period include strength, application timing, and the like. The length of the recovery period from the end of the echo train to the next TR can be adjusted by adjusting the imaging parameter TR. Details of the adjustment will be described later.

The sequence creating section 710 of the present embodiment receives an imaging parameter from the user, and causes the parameter adjusting section 711 to adjust the adjustment parameter using the imaging parameter. A default value may be set for the imaging parameter. In this case, the adjustment parameter after the adjustment (optimal value) may be automatically reflected in the imaging sequence, or may just be presented to the user. In this case, the optimal value after the adjustment may be reflected when the instruction of comprehension for the optimal value after the adjustment is received from the user, or the parameter after the adjustment may be just presented so that a further adjustment is received from the user.

FIG. 5 (a) shows an imaging parameter input screen 400 that is generated by the sequence creating section 710 when the imaging parameter is received from the user and is displayed on the display device 173. The imaging parameter input screen 400 includes an imaging parameter setting region 410 to receive an input of the imaging parameter from the user or display the set parameter and a determination button 420 to receive an instruction to start imaging using the imaging parameter input through the imaging parameter setting region 410.

In addition, the adjustment result of the adjustment parameter may just be presented to the user. In this case, the imaging parameter setting region 410 includes an adjustment parameter input region 401 to receive an input of the adjustment parameter and an adjustment parameter display region 402 to display the adjustment result for the adjustment parameter. In addition, a button to reflect the adjustment result (reflection button) 404 may also be provided. In this diagram, a case in which TR is used as an adjustment parameter is illustrated. In this case, when the input of imaging parameters including the adjustment parameter from the user is received through the imaging parameter setting region 410, the sequence creating section 710 causes the parameter adjusting section 711 to adjust the adjustment parameters and displays the adjustment result in the adjustment parameter display region 402.

The user views the display, and determines whether to perform imaging using the adjustment parameters after the adjustment or to change the adjustment parameters. Then, in the case of performing imaging using the adjustment parameters after the adjustment that are displayed, the user presses the reflection button 404. When the pressing of the reflection button 404 is received from the user, the value of the adjustment parameter display region 402 is input to the adjustment parameter input region 401. In addition, when the pressing of the determination button 420 is received from the user, the sequence creating section 710 generates an imaging sequence using the parameters set in the adjustment parameter input region 401 and other imaging parameters.

On the other hand, in the case of changing the adjustment parameters freely, the user inputs each desired value to the adjustment parameter input region 401. The sequence creating section 710 causes the parameter adjusting section 711 to adjust each adjustment parameter whenever the value is input to the adjustment parameter input region 401.

In addition, in the case of reflecting the adjustment result of adjustment parameters automatically in the imaging sequence, the adjustment parameter input region 401 and the reflection button 404 may not be provided. The sequence creating section 710 receives an input of imaging parameters from the user through the imaging parameter setting region 410, and causes the parameter adjusting section 711 to adjust the adjustment parameters. Then, when the pressing of the determination button 420 is received, an imaging sequence is generated using the adjustment parameters after the adjustment and other imaging parameters.

When there are several adjustment methods in the adjustment of contrast, a contrast adjustment setting region 403 to designate a contrast adjustment method may be provided in the imaging parameter setting region 410, as shown in FIG. 5(b). The user designates an adjustment method through the contrast adjustment setting region 403 to designate a contrast adjustment method. For example, the contrast adjustment method designated by the user is an image type to be acquired, such as T2-weighted image acquisition or T1-weighted image acquisition. For example, T2 is designated when a T2-weighted image needs to be acquired, and T1 is designated when a T1-weighted image needs to be acquired. When T2 is designated, the sequence creating section 710 causes the parameter adjusting section 711 to adjust the imaging parameters so that the influence of T1 is reduced. On the other hand, when T1 is designated, the sequence creating section 710 causes the parameter adjusting section 711 to adjust the imaging parameters so that the influence of T2 is reduced.

In addition, an instruction regarding whether to set the TR automatically or to just present the optimal TR may be given through the contrast adjustment setting region 403.

Next, details of the process of adjusting the adjustment parameter by the parameter adjusting section 711 of the present embodiment will be described. As described above, the parameter adjusting section 711 of the present embodiment adjusts the adjustment parameter using the signal strengths of echo signals arranged at the k-space center, among echo signals from a plurality of tissues having different combinations of T1 and T2. When T2 is the same, adjustment is performed so that the signal strength difference is reduced even if T1 is different.

Figure 6:
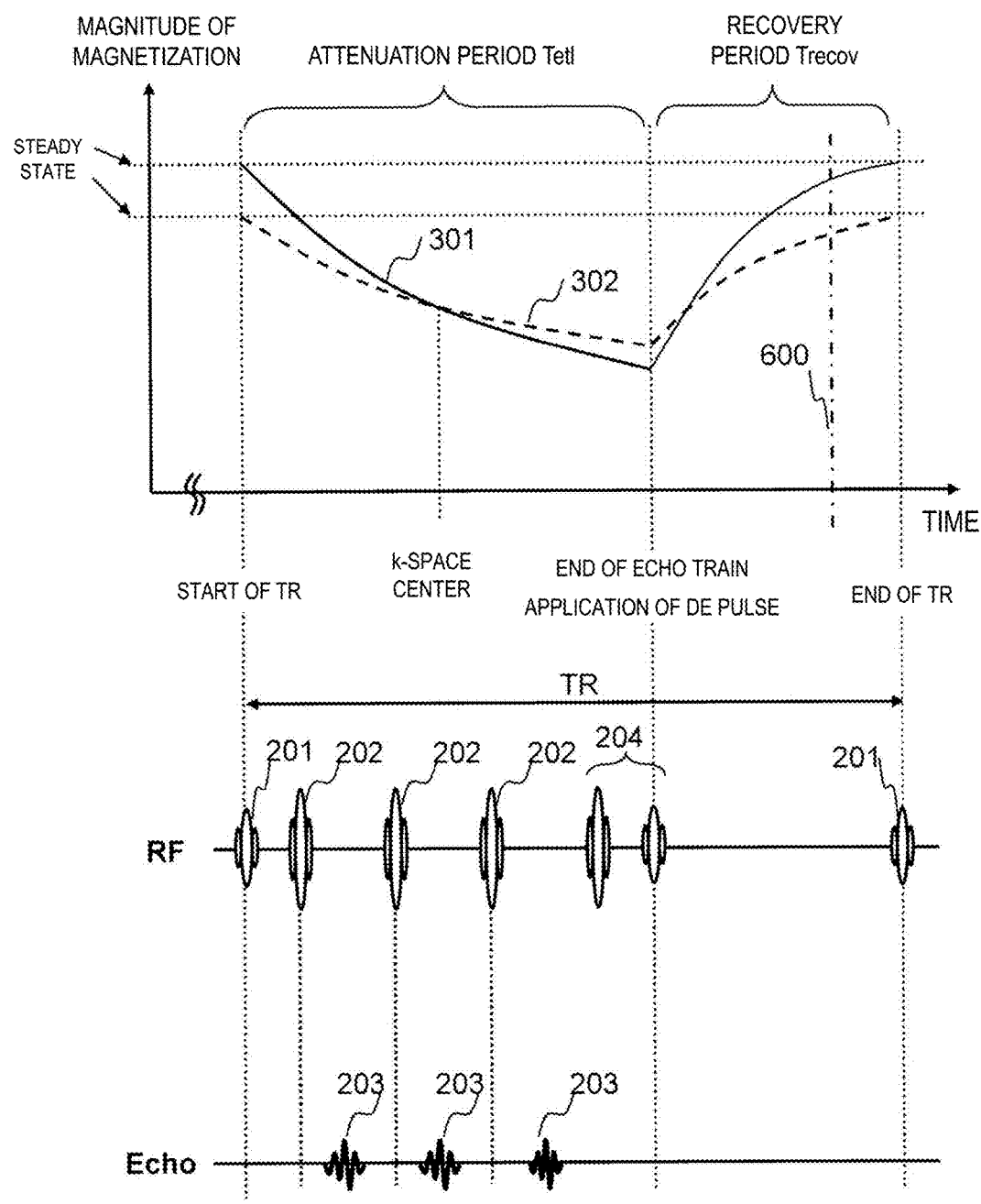
FIG. 6 is a diagram for explaining the adjustment process in the first embodiment.

As an example, FIG. 6 shows changes in the magnitude of magnetization of two tissues A and B having the same T2 and different T1, application timing of the RF pulse, and acquisition timing of the echo signal. Tissues of such T1 and T2 do not need to be present in practice. This is an example for explaining the influence of T1 and T2. Similarly, tissues used in the following explanation are examples.

Here, the VRFA sequence 200 shown in FIG. 3 is used as a pulse sequence.

In addition, as described above, the sequence to be used is not limited to the VRFA sequence 200. Any sequence may be used in which the FA of at least one refocus RF pulse 202 is not 180°.

It is assumed that the longitudinal relaxation time T1A of the tissue A is shorter than the longitudinal relaxation time T1B of the tissue B (T1A<T1B). The solid line 301 shows a change in the magnitude of magnetization of the tissue A, and the broken line 302 shows a change in the magnitude of magnetization of the tissue B. Only the magnitude of magnetization that contributes to the echo signal to be acquired is shown. In addition, a change within 1 TR when the VRFA sequence 200 is sufficiently repeated to realize a steady state is shown.

In the case of using the VRFA sequence 200, as shown in this diagram, when excitation occurs due to the excitation RF pulse 201 after the start of the TR, the magnitudes 301 and 302 of magnetization of both the tissues A and B change until the end of the echo train while refocusing due to the refocus RF pulse 202 occurs. The changes 301 and 302 in the magnitudes of magnetization include T1 attenuation of longitudinal magnetization occurring due to the FA of the refocus RF pulse 202 that is not 180°. This period will be referred to as an attenuation period (Tet1).

Here, when the DE pulse 204 is applied after the acquisition of the last echo signal of the echo train, magnetization that contributes to the echo signal to be acquired becomes longitudinal magnetization, thereby realizing the T1 recovery until the end of the TR. This period will be referred to as a recovery period (Trecov). The recovered longitudinal magnetization contributes to echo signals to be acquired in the next TR. That is, in the next TR, a change is started from the magnitude of magnetization recovered at the end of the last TR. Therefore, the magnitude of magnetization at the end of the TR can be set to the magnitude of magnetization at the start of the next TR, which is optimal in the next TR, by adjusting the degree of recovery of magnetization in the recovery period.

When only the two tissues A and B are taken into consideration, the magnitude of the optimal magnetization at the end of the TR is when the magnitudes (signal strengths) of magnetization of the tissues A and B become approximately equal at a timing, at which the k-space center to determine the contrast is acquired, in the next TR.

Therefore, the parameter adjusting section 711 adjusts the adjustment parameters so that the variance Scvar of each signal strength Sc is minimized, as a state in which the signal strengths Sc at the k-space center in the steady state in a plurality of tissues having the same T2 and different T1 are approximately equal. That is, the parameter adjusting section 711 of the present embodiment sets the variance Scvar as an objective function, searches for an adjustment parameter that minimizes the objective function, and determines the adjustment parameter as an optimal value.

Hereinafter, a case in which the adjustment parameter is TR will be described as an example. In the present embodiment, the adjustment of the TR is realized by adjusting a period from the application of the DE pulse 204 to the start of the next TR (recovery period Trecov). As shown in FIG. 6, the TR is a sum of the attenuation period (Tet1) from the application of the excitation RF pulse 201 to the application of the DE pulse 204 and the recovery period Trecov. In this example, the attenuation period Tet1 is fixed. Therefore, adjusting the recovery period Trecov means adjusting the TR.

A specific method of the above adjustment of the parameter adjusting section 711 will be described below. Assuming that T1 of each of N (N is an integer of 2 or more) tissues having the same T2 and different T1 is T1(n) (n=1, 2, 3, . . . , N) and the signal strength at the k-space center in the steady state of T1(n) is Sc(n), the objective function is the variance Scvar of "N" Sc(n). The parameter adjusting section 711 of the present embodiment determines an adjustment parameter TR (here, Trecov) that minimizes the objective function Scvar.

Equations required to calculate Sc(n) are shown below. The magnitude MTend of transverse magnetization at the end of the echo train (immediately before the application of the DE pulse), the magnitude MLde of longitudinal magnetization after the application of the DE pulse 204, the magnitude MT0 of transverse magnetization immediately after excitation, and the signal strength Sc(n) will be described with reference to the following four separate Equations (1) to (4).

$$MTend = MT0 \times Rend(n) \qquad (1)$$

$$MLde = MTend \times \sin(-FAde) \qquad (2)$$

$$MT0 = 1 - (1 - MLde) \times \exp(-Trecov/T1(n)) \qquad (3)$$

$$Sc(n) = MT0 \times Rcent(n) \qquad (4)$$

Here, the magnitude of magnetization immediately after excitation after complete recovery is set to 1. Rend(n) is the ratio of the magnitude of transverse magnetization at the end of the echo train to that at the start of the echo train when T1 is T1(n), and can be calculated using the Bloch equation from the FA and T1 and T2 of the refocus RF pulse 202. FAde is the FA of the second pulse of the DE pulse 204. This is assumed to have the same phase as the excitation pulse (negative at the time of flip-back). Trecov is a time from the application of the DE pulse 204 to the application of the next excitation RF pulse 201 as described above. Rcent(n) is the ratio of the magnitude of transverse magnetization at the time of k-space center collection to the magnitude of transverse magnetization at the start of the echo train when T1 is T1(n), and can be calculated using the Bloch equation from the FA and T1 and T2 of the refocus RF pulse 202. In addition, the timing to collect echo signals arranged at the k-space center can be arbitrarily changed by echo shift or the like.

By solving Equations (1) to (3), MT0 in the steady state is expressed with Rend(n), FAde, Trecov, and T1(n). In addition, Sc(n) is calculated by substituting the obtained MT0 into Equation (4).

When the DE pulse 204 is not applied, the FA of the DE pulse 204 is set to 0, and the end of the Tet1 and the start of the Trecov are not the DE pulse but the last pulse of the echo train. In the example described above, the magnitude of longitudinal magnetization MLend at the end of the echo train (immediately before the application of the DE pulse 204) is set to 0 for the sake of simplicity. When longitudinal magnetization Mlend at the end of the echo train is taken into consideration, the longitudinal magnetization component of the MTend is also taken into consideration by adding the longitudinal magnetization version (1-1) of Equation (1) and replacing Equation (2) with Equation (2-1).

$$MLend = MT0 \times RLend(n) + CLend(n) \qquad (1\text{-}1)$$

$$MLde = MTend \times \sin(-FAde) + MLend \times \cos(FAde) \qquad (2\text{-}1)$$

Here, RLend(n) and CLend(n) are coefficients when Equation expressing a change in the longitudinal magnetization within the echo train when T1 is T1(n) is rearranged with respect to MT0.

The parameter adjusting section 711 searches for an adjustment parameter, which minimizes the objective function (Scvar), while changing the adjustment parameter TR (here, Trecov that determines the TR). A general optimization method can be used for the search. For example, it is possible to use a method of searching for an adjustment parameter, which minimizes the objective function, while changing the adjustment parameter according to a bisection method of searching for an adjustment parameter minimizing the objective function using a steepest descent method with the adjustment parameter set by the user as an initial value.

A general method can be used for the convergence determination. For example, it is possible to use a method of repeating the search a predetermined number of times (M times) or a method of repeating the search until the change in the objective function becomes sufficiently small.

The parameter adjusting section 711 searches for an adjustment parameter that minimizes the objective function, and outputs the TR determined from the search result as an adjustment result (optimal value).

The method of the adjustment performed by the parameter adjusting section 711 will be shown as a specific example. FIGS. 7(a) and 7(b) are diagrams for explaining the specific example of parameter adjustment, and are graphs showing changes in the signal strength Sc at the k-space center in the steady state in three tissues, which have the same T2 and different T1, according to the TR. Three T1(T1(1), T1(2), T1(3)) are set to T1(1)=500 ms, T1(2)=800 ms, and T1(3)=1000 ms. FIG. 7(a) is a graph showing a signal strength change in the tissue having T2 of 50 ms, and FIG. 7(b) is a graph showing a signal strength change in the tissue having T2 of 100 ms. Here, the number of echo trains (ETL) is set to 80, and an echo interval (IET) is set to 7.3 ms. The FA of the refocus RF pulse 202 is changed according to the FA change shape FAP shown in FIG. 4. The DE pulse 204 is not applied (FA is 0°).

As shown in FIG. 7 (a), in the case of the tissue having T2 of 50 ms, it can be seen that the TR (optimal value) minimizing the variance Scvar of the Sc is approximately 1.75 seconds. On the other hand, as shown in FIG. 7(b), in the case of the tissue having T2 of 100 ms, it can be seen that the TR (optimal value) minimizing the variance Scvar of the Sc is approximately 1.85 seconds similarly.

Figure 8:
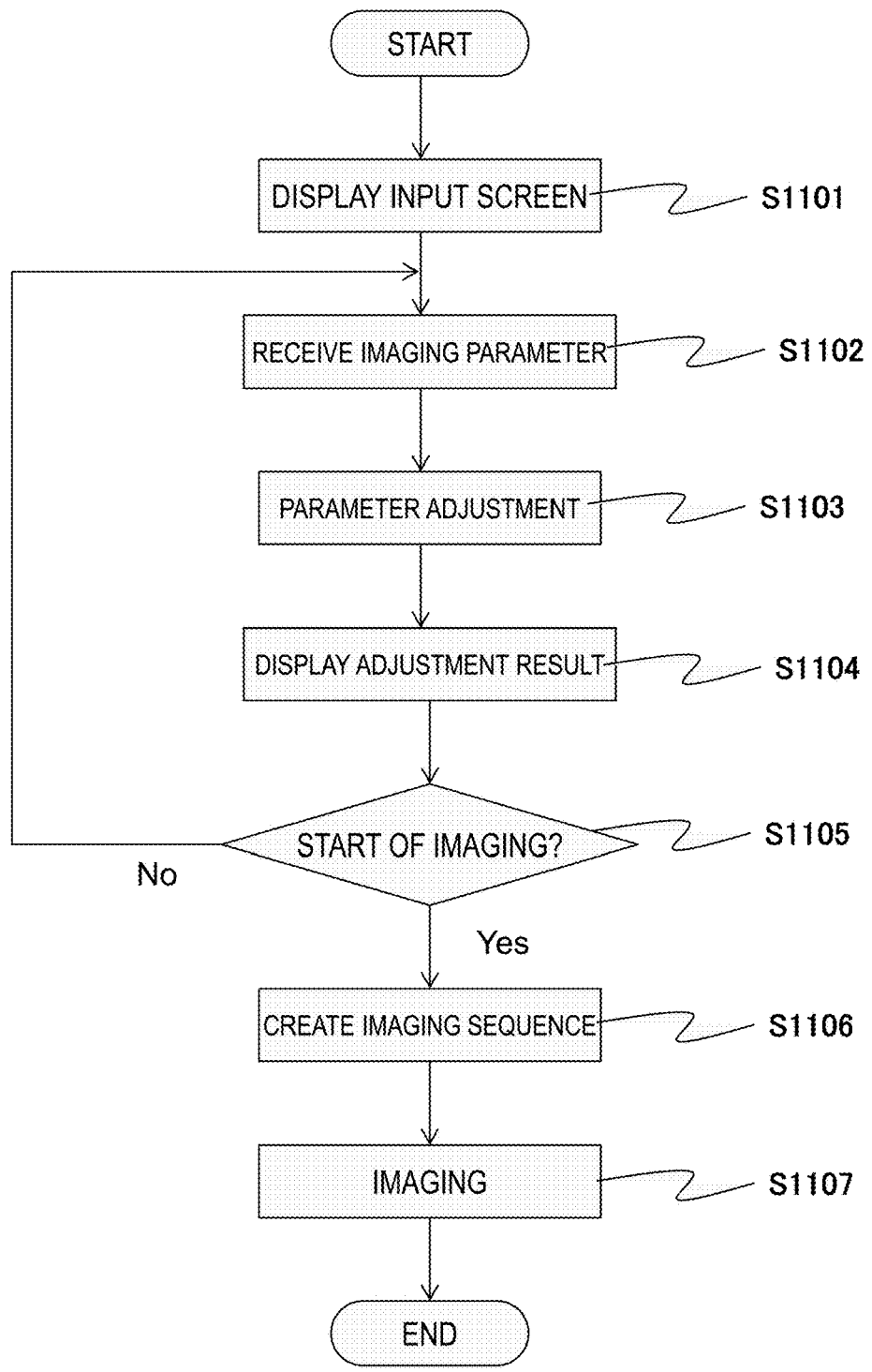
FIG. 8 is a flowchart of the imaging process in the first embodiment.

Next, the flow of the imaging process performed by the control unit 170 of the present embodiment will be described. FIG. 8 is a process flow of the imaging process of the present embodiment. Here, a case is illustrated in which the sequence creating section 710 adjusts an imaging parameter, presents the imaging parameter to the user after adjusting, and eventually generates an imaging sequence with the imaging parameter set by the user. The imaging process is started by receiving the start instruction from the user.

The sequence creating section 710 displays the imaging parameter input screen 400 on the display device 173 (step S1101), and waits for an input from the user. When the input of an imaging parameter is received from the user (step S1102), the parameter adjusting section 711 performs a parameter adjustment process for adjusting the adjustment parameter set in advance using the above-described method (step S1103). For example, when the adjustment parameter is TR and T2 weighting is designated as an imaging parameter to set the adjustment method, an optimal TR to reduce the T1 contrast is determined.

The sequence creating section 710 displays the adjustment result (optimal value) of the parameter adjusting section 711 (step S1104). Here, the adjustment result (optimal value) of the parameter adjusting section 711 is displayed in the adjustment parameter display region 402 of the imaging parameter input screen 400.

Then, the sequence creating section 710 waits for an instruction to start imaging from the user through the imaging parameter input screen 400. When the instruction to start imaging is received (step S1105), the sequence creating section 710 create an imaging sequence using the imaging parameter at that point in time (step S1106). Then, the imaging section 720 performs imaging according to the imaging sequence (step S1107).

On the other hand, in step S1105, when an input, such as an imaging parameter change, is received from the user during the waiting, the sequence creating section 710 returns to step S1102 to repeat the processing. Thus, the user can also change the adjustment parameter with reference to the optimal value of the displayed adjustment parameter until the user gives an instruction to start imaging.

Figure 9:
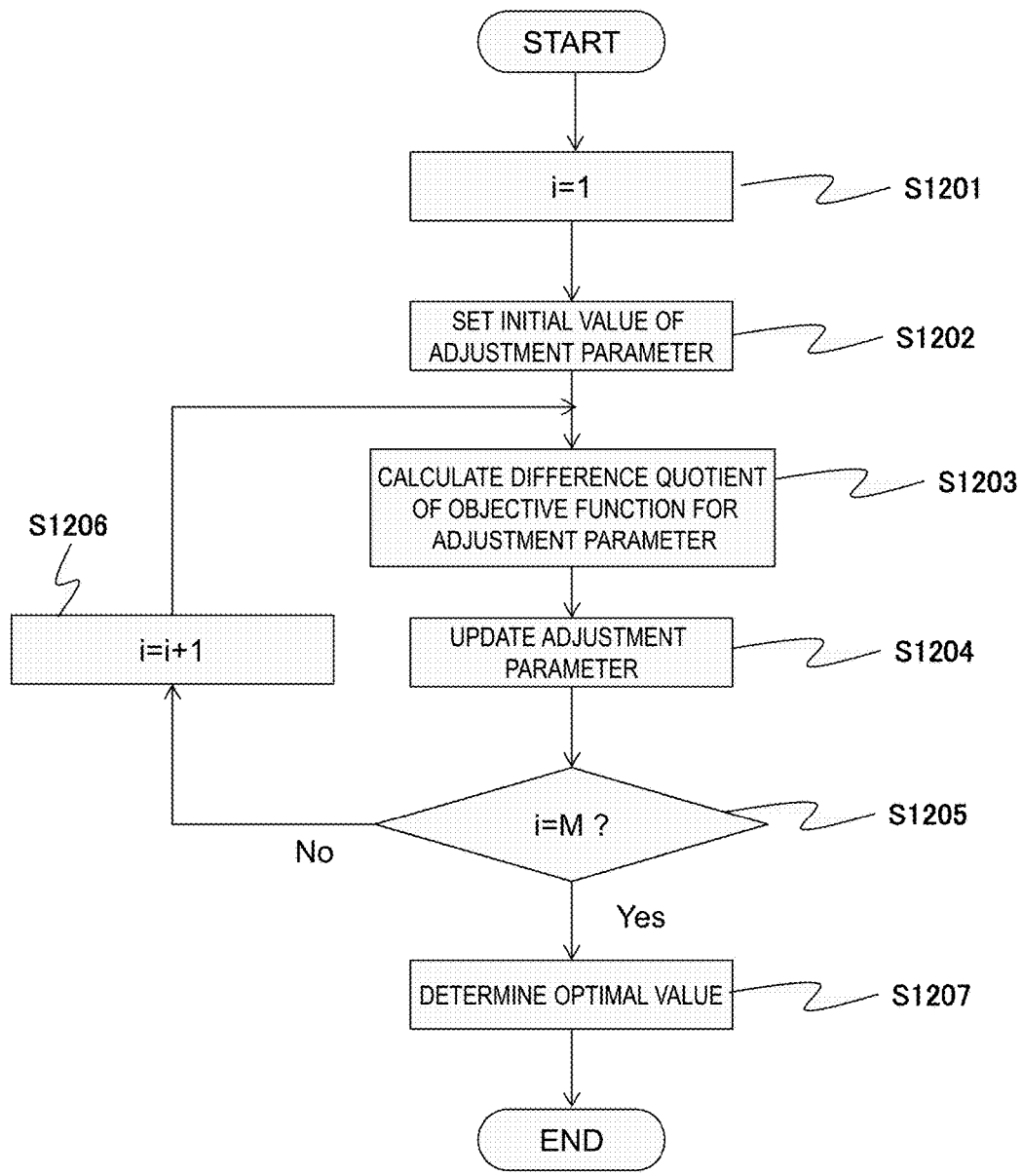
FIG. 9 is a flowchart of the parameter adjustment process in the first embodiment.

Next, an example of the flow of the parameter adjustment process performed by the parameter adjusting section 711 in the above step S1103 will be described. FIG. 9 is a process flow of the parameter adjustment process of the present embodiment.

Here, a target imaging parameter is set to TR. In addition, it is assumed that the adjustment parameter is updated M times. The adjustment parameter that has been updated i times is expressed as TR(i), and the objective function Scvar obtained by TR(i) is expressed as f(TR(i)).

The counter i to count the number of updates is initialized (i=0) (step S1201). Then, the value input by the user is set to the initial value (TR(0)) of the adjustment parameter (step S1202).

Then, using the value of the adjustment parameter at that point in time, a difference quotient ($\Delta f(TRW)/h$) of the objective function f(TR(i)) is calculated (step S1203). Here, $\Delta f(TR(i))$ is $f(TR(i)+h)-f(TR(i))$. h is a sufficiently small value, and is appropriately determined so as to be satisfactorily used in the steepest descent method. For example, h is set to $1/1000$ of TR(0). Alternatively, h may be determined according to the accuracy that can be set for the TR.

Then, using the obtained difference quotient, the adjustment parameter TR(i) is updated (step 1204). Specifically, the adjustment parameter TR(i) is updated by calculating $TR(i)=TR(i-1)-\alpha\times(\Delta f(TR(i))/h)$. Here, a is a small number set in advance. $\alpha$ is appropriately determined by a method that is performed satisfactorily in the steepest descent method. For example, $\alpha$ is set to $1/(\Delta f(TR(0)/h)\times TR(0)/1000$. Alternatively, $\alpha$ may be experientially determined so as to realize good convergence by checking the change in the objective function f(TR(i)) in some cases.

The processing of steps S1203 and S1204 described above is repeated M times (steps S1205 and S1206). Then, an adjustment parameter TR(M) after repeating the processing of steps S1203 and S1204 M times is determined as an optimal value (step S1207), and the process is ended.

In the parameter adjustment process described above, a search range may be set when adjusting the adjustment parameter. That is, the adjustable range of the adjustment parameter, specifically, a range (variation range) to change the value of the adjustment parameter, may be limited.

For example, in the examples shown in FIGS. 7 (a) and 7 (b), TR that minimizes the variance Scvar of the signal strength is 0.6 seconds. This is the TR at which the signal strength Sc of each of T1(1), T1(2), and T1(3) becomes 0, and a case in which the Trecov is 0. At this point in time, T1 recovery has not been made at all, and no signal is generated thereafter. Therefore, this is a meaningless setting in practice. In order to avoid the calculation of such a TR, for example, a limit equal to or greater than 1 second is set for the TR variation range.

In addition, the imaging time increases as the TR increases. For this reason, a limit on the TR variation range may be set in order to optimize the contrast in the range. For example, TR is limited to 10 seconds or less.

Figure 10:
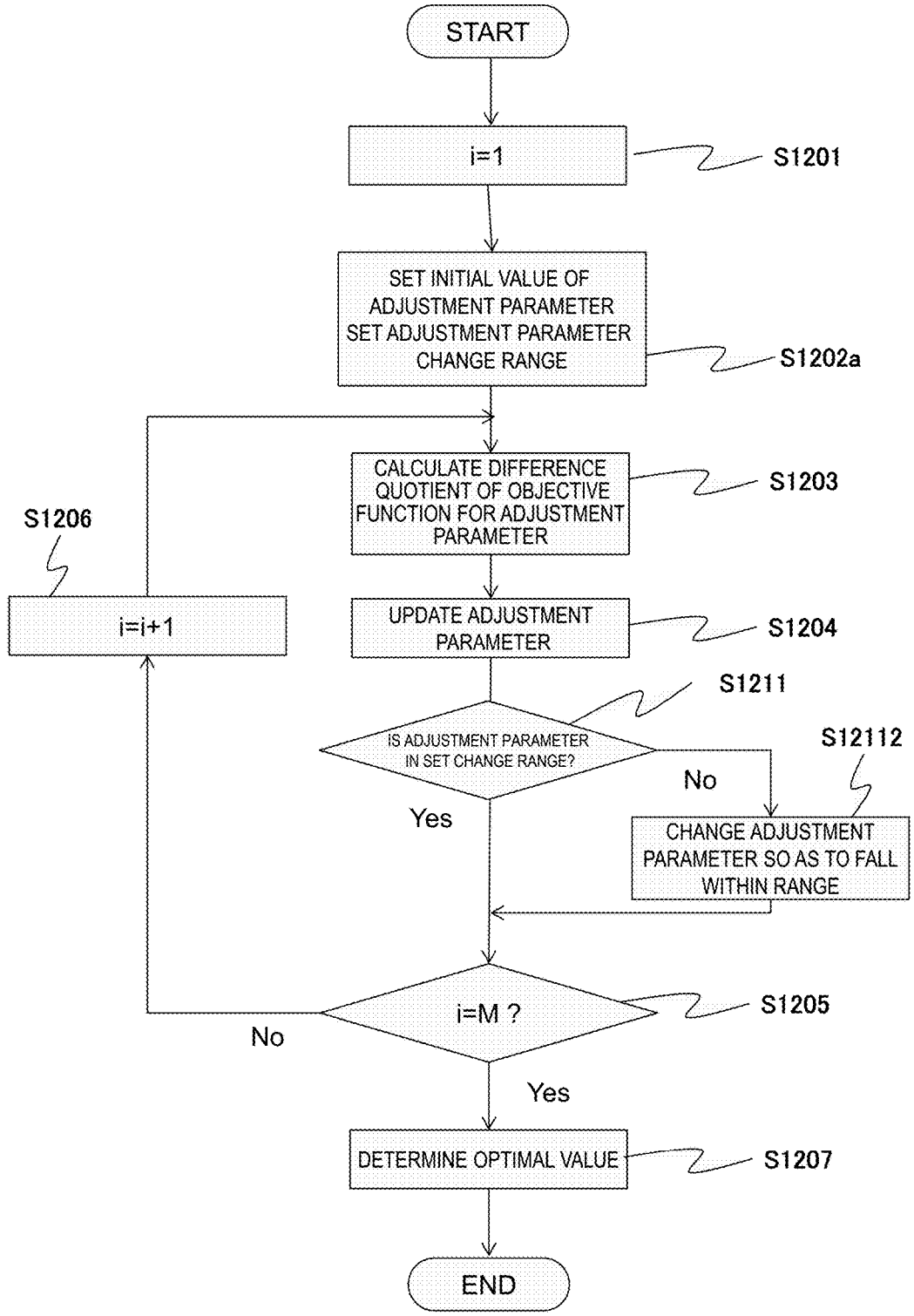
FIG. 10 is a flowchart of a modification example of the parameter adjustment process in the first embodiment.

FIG. 10 shows the process flow of the parameter adjustment process when a limit is set on the range (variation range) where the change in the value of the adjustment parameter is allowed. This is basically the same as the process flow of the parameter adjustment process shown in FIG. 9. However, the difference is that the variation range of the value of the adjustment parameter is set at the time of initial setting and that the value of the adjustment parameter is changed within the set variation range.

In this example, as shown in FIG. 10, in step S1202a, when setting the initial value of the adjustment parameter, the variation range of the value of the adjustment parameter is also set. After updating the adjustment parameter in step S1204, it is determined whether or not the adjustment parameter after the updating is within the range set in step S1202a (step S1211). If the adjustment parameter after the updating is within the range, the process proceeds to step S1205. On the other hand, if the adjustment parameter after the updating is outside of the range, the adjustment parameter is changed to the closest value in the variation range (step S1212).

In the above embodiment, the case in which the TR is set as an adjustment parameter in the adjustment when capturing the T2-weighted image has been described as an example. However, as described above, the adjustment parameter that is adjusted when capturing the T2-weighted image is not limited thereto. An imaging parameter that affects T1 recovery or T1 attenuation may also be used.

The application parameter of the RF pulse or the gradient magnetic field that is applied during the recovery period Trecov from the application of the last refocus RF pulse of the echo train to the next excitation RF pulse 201 can be used as an adjustment parameter.

For example, as described above, the FA of the DE pulse 204, a saturation pulse, the FA of each of one or more RF applied during Trecov that is the recovery period, the strength of the gradient magnetic field pulse applied during Trecov, and a combination thereof may also be used as adjustment parameters.

In addition, for example, the FA of VRFA, an echo shift, and the like may also be set as adjustment parameters. It is difficult to handle the FA or the echo shift since the FA or the echo shift also changes the influence of T2, but the FA or the echo shift can be used for adjustment in order to change the influence of T1.

Figure 11:
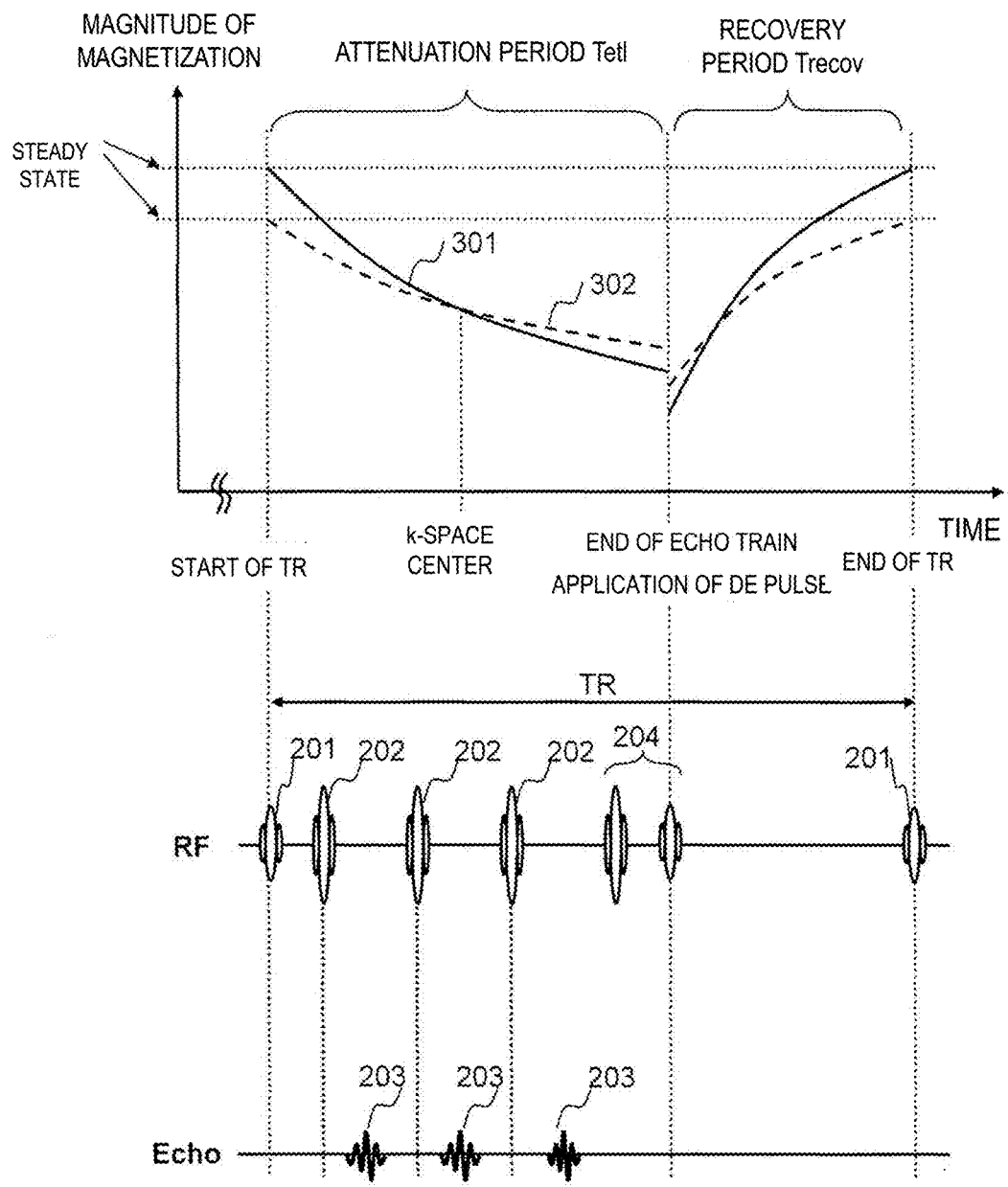
FIG. 11 is a diagram for explaining the overview of the adjustment process when the adjustment parameter is a flip angle of a DE pulse in the first embodiment.

For example, the overview of adjustment processing when the adjustment parameter at the time of capturing of the T2-weighted image is the FA of the DE pulse 204 will be described with reference to FIG. 11. Similar to FIG. 6, FIG. 11 shows changes in the magnitude of magnetization of two tissues A and B having the same T2 and different T1, application timing of the RF pulse, and acquisition timing of the echo signal.

The pulse sequence to be used is, for example, the VRFA sequence 200, and the relationship of T1(T1A and TiB) between the tissues A and B is assumed to be T1A<T1B. The solid line 301 shows a change in the magnitude of magnetization of the tissue A, and the broken line 302 shows a change in the magnitude of magnetization of the tissue B. Only the magnitude of magnetization that contributes to the echo signal to be acquired is shown. In addition, a change within 1 TR when the VRFA sequence 200 is sufficiently repeated to realize a steady state is shown.

Here, when the DE pulse 204 is applied after the acquisition of the last echo signal of the echo train, magnetization that contributes to the echo signal to be acquired becomes longitudinal magnetization, thereby realizing the T1 recovery until the end of the TR. In this case, as shown in FIG. 11, the magnitude of magnetization at the start of the recovery period Trecov is changed by changing the FA of the DE pulse 204. Therefore, it is possible to adjust the degree of recovery of the magnetization. That is, the parameter adjusting section 711 can optimize the magnitude of magnetization at the end of the TR by adjusting the FA of the DE pulse 204. Also in this case, the magnitude of the optimal magnetization at the end of the TR is when the magnitudes (signal strengths) of magnetization of the tissues A and B become approximately equal at a timing, at which the k-space center to determine the contrast is acquired, in the next TR.

The signal strength $Sc(n)$ can be calculated from Equations (1) to (4), as in the case in which the TR is set to the adjustment parameter. Similar to the case in which the TR is set to the adjustment parameter, the parameter adjusting section 711 adjusts the adjustment parameter so as to minimize the objective function (Scvar) while changing the FA (FAde) of the DE pulse 204. The only difference is that the adjustment parameter is FAde.

In addition, the application timing of the saturation pulse may be set as the adjustment parameter when capturing the T2-weighted image. The saturation pulse is typically an RF pulse that is applied in order to suppress a signal from a specific component or location. Here, the saturation pulse is used in the meaning of an RF pulse that is applied between echo trains in order to suppress the signal. There is no need to be limited to a specific component or location. Typically, the gradient magnetic field is also applied in order to eliminate the signal. In the present embodiment, however, since it is sufficient to apply the gradient magnetic field so as to eliminate the signal, only the method of applying the RF pulse will be described herein.

Figure 12:
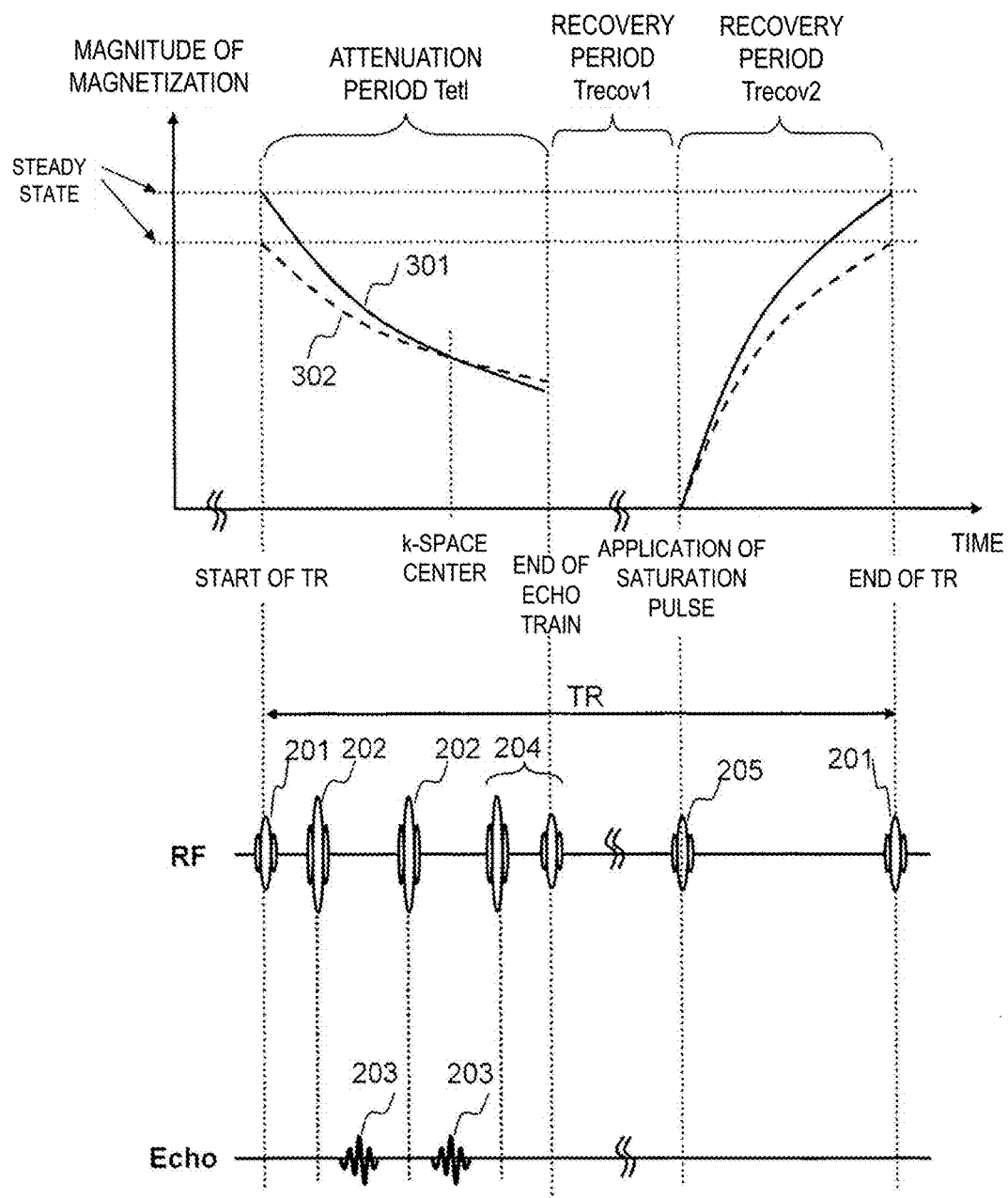
FIG. 12 is a diagram for explaining the overview of the adjustment process when the adjustment parameter is the application timing of a saturation pulse in the first embodiment.

The overview of the parameter adjustment process in this case will be described with reference to FIG. 12. Similar to FIG. 6, FIG. 12 shows changes in the magnitude of magnetization of two tissues A and B having the same T2 and different T1, application timing of the RF pulse, and acquisition timing of the echo signal.

The pulse sequence to be used is, for example, the VRFA sequence 200, and the relationship of T1 (T1A and T1B) between the tissues A and B is assumed to be T1A<T1B. The solid line 301 shows a change in the magnitude of magnetization of the tissue A, and the broken line 302 shows a change in the magnitude of magnetization of the tissue B. Only the magnitude of magnetization that contributes to the echo signal to be acquired is shown. In addition, a change within 1 TR when the VRFA sequence 200 is sufficiently repeated to realize a steady state is shown.

Here, when a saturation pulse 205 is applied at a predetermined timing in the echo train, that is, in the Trecov, magnetization that contributes to the echo signal to be acquired is eliminated, thereby realizing the T1 recovery until the end of the TR from the application of the saturation pulse 205. In this case, as shown in FIG. 12, the degree of recovery of magnetization can be adjusted by changing the application timing of the saturation pulse 205. That is, the parameter adjusting section 711 can optimize the magnitude of magnetization at the end of TR by adjusting the application timing of the saturation pulse 205. Also in this case, the magnitude of the optimal magnetization at the end of the TR is when the magnitudes (signal strengths) of magnetization of the tissues A and B become approximately equal at a timing, at which the k-space center to determine the contrast is acquired, in the next TR.

In this case, the parameter adjusting section 711 calculates an optimal value by replacing the above Equation (3) with the following Equations (5) and (6).

$$M\text{sat}{-}1{-}(1{-}ML{de}\mathrm{exp}(-T\text{recov}1/T1(n))) \quad (5)$$

$$MT0{=}1{-}(1{-}M\text{sat}\times\cos(FA\text{sat}))\times\mathrm{exp}(-T\text{recov}2/T1(n)) \quad (6)$$

Here, Msat is the magnitude of magnetization immediately before the application of the saturation pulse 205, FAsat is the FA of the saturation pulse 205, Trecov1 is a time from the DE pulse 204 to the application of the saturation pulse 205, and Trecov2 is a time from the saturation pulse 205 to the start of the next echo train.

By solving Equations (1), (2), (5), and (6), MT0 in the steady state is expressed with Rend(n), FAde, FAsat, Trecov1, Trecov2, and T1(n). In addition, Sc(n) is calculated by substituting the MT0 into Equation (4). Similar to the case in which the TR is set to the adjustment parameter, the parameter adjusting section 711 adjusts the adjustment parameter so as to minimize the objective function (Scvar) while changing the Trecov2. The only difference is that the adjustment parameter is Trecov2.

By setting the saturation pulse 205 as an adjustment parameter, it is possible to set the magnetization to 0 at a desired timing. Therefore, it is possible to realize the desired T1 recovery regardless of the length of the TR. For example, even if the TR is long, the degree of T1 recovery can be suppressed by delaying the application timing of the saturation pulse 205. Therefore, this is useful for imaging in which it is not possible to designate a short TR, such as synchronous measurement. In addition, FAsat may be set as an adjustment parameter.

Until now, the case of performing adjustment as adjustment parameters using one of the variables appearing in Equations (1) to (6) has been described as an example of the adjustment method. However, as described above, the number of adjustment parameters is not limited to one. A plurality of adjustment parameters may be combined to perform adjustment.

For example, the length of the recovery period Trecov, an RF waveform applied during the Trecov, and a gradient magnetic field strength applied during the Trecov can be used as adjustment parameters. Here, the RF waveform applied during the Trecov is determined by the FA value column of the RF pulse for flip-back/down applied during the Trecov. One or more imaging parameters of these are used as adjustment parameters.

Figure 13:
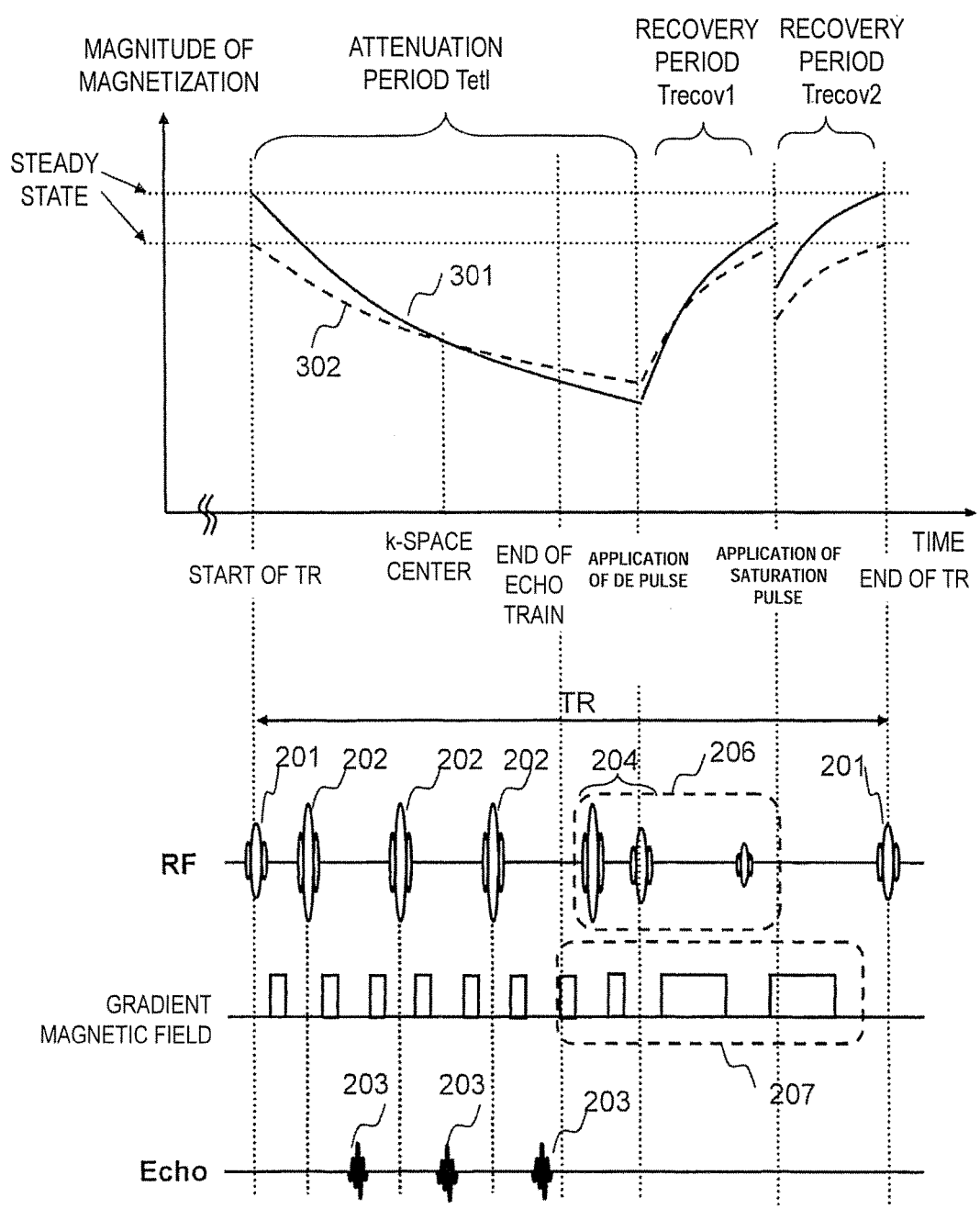
FIG. 13 is a diagram for explaining the overview of the adjustment process when the adjustment parameter is a combination of a plurality of imaging parameters in the first embodiment.

The overview when all of these adjustment parameters are combined to perform adjustment will be described with reference to FIG. 13. Similar to FIG. 6, FIG. 13 shows changes in the magnitude of magnetization of two tissues A and B having the same T2 and different T1, application timing of the RF pulse, application timing of the gradient magnetic field, and acquisition timing of the echo signal.

The pulse sequence to be used is, for example, the VRFA sequence 200, and the relationship of T1 (T1A and T1B) between the tissues A and B is assumed to be T1A<T1B. The solid line 301 shows a change in the magnitude of magnetization of the tissue A, and the broken line 302 shows a change in the magnitude of magnetization of the tissue B. Only the magnitude of magnetization that contributes to the echo signal to be acquired is shown. In addition, a change within 1 TR when the VRFA sequence 200 is sufficiently repeated to realize a steady state is shown.

Here, when the DE pulse 204 is applied after the acquisition of the last echo signal of the echo train, magnetization that contributes to the echo signal to be acquired becomes longitudinal magnetization, thereby realizing the T1 recovery until the end of the TR. The degree of recovery of magnetization is adjusted by adjusting the recovery period Trecov, or applying an RF pulse waveform 206 during the recovery period Trecov, or applying a gradient magnetic field 207. The magnitude of the optimal magnetization at the end of the TR is when the magnitudes (signal strengths) of magnetization of the tissues A and B become approximately equal at a timing, at which the k-space center to determine the contrast is acquired, in the next TR.

More generally, it is possible to adjust all sequence shapes, such as the application timing, the RF waveform, and the gradient magnetic field strength, as adjustment parameters. The example described so far is an example of adjusting some of them. For example, in the above example in which TR is an adjustment parameter, the RF waveform and the gradient magnetic field strength are fixed, and only the last waiting time of the application timing is set as an adjustment parameter. In addition, in the example in which the FA of the DE pulse 204 and the FA of the saturation pulse 205 are adjustment parameters, the application timing and the gradient magnetic field strength are fixed, and only the strength of some pulses of the RF waveform is set as an adjustment parameter.

Here, when most generalized, the magnitude of echo signals arranged at the k-space center to determine the contrast is calculated using the Bloch equation showing in the following equation (7). A general calculation method is used. For example, when the gradient magnetic field is taken into consideration, it is preferable to solve the equation for the respective gradient magnetic field application directions and add the results. In order to obtain the steady state, it is preferable to repeat the above for a sufficient period of time. A desired variable among variables included in this equation may be set as an adjustment parameter.

$$\frac{d\vec{M}}{dt} = \gamma \vec{M} \times \vec{B}_{ext} + \frac{1}{T_1}(M_0 - M_z)\hat{z} - \frac{1}{T_2}\vec{M}_\perp \quad (7)$$

γ: magnetic rotation ratio
$\vec{M}$: magnetization
$\vec{B}_{ext}$: external magnetic field
$M_z$: z component of magnetization
$M_0$: $M_z$ of thermal equilibrium
$\hat{z}$: unit vector in z direction (static magnetic field direction)
$M_\perp$: transverse magnetization Also in this case, imaging parameters may be adjusted with a simple equation obtained by limiting the Trecov period, the RF waveform, and the gradient magnetic field strength to some extent, instead of directly solving the Bloch equation shown in Equation (7).

Even if any of the imaging parameters is set as an adjustment parameter, a variation range may be set and adjustment may be performed within the range.

In the embodiment described above, the optimal adjustment parameter is determined using the signal strength Sc at the k-space center in the tissues having different T1 for one T2. However, a plurality of T2 that is taken into consideration when determining the adjustment parameter may be used.

In this case, the objective function is assumed to be a sum of coefficients of variation (variance/average) of the signal strength Sc with respect to the respective T2 values. When two T2 ($T2_1$ and $T2_2$) are taken into consideration, the above-described parameter adjustment process is performed by using $Sccv_1 + Sccv_2$ as an objective function. $Sccv_1 + Sccv_2$ is a sum of a coefficient of variation $Sccv_1$ of the signal strength at the k-space center obtained by using a plurality of tissues having different T1 when T2 is $T2_1$ and a variance $Sccv_2$ of the signal strength at the k-space center obtained by using a plurality of tissues having different T1 when T2 is $T2_2$. The flow of the process in this case is the same as that of the parameter adjustment process described with reference to FIG. 9 or 10.

Figure 14:
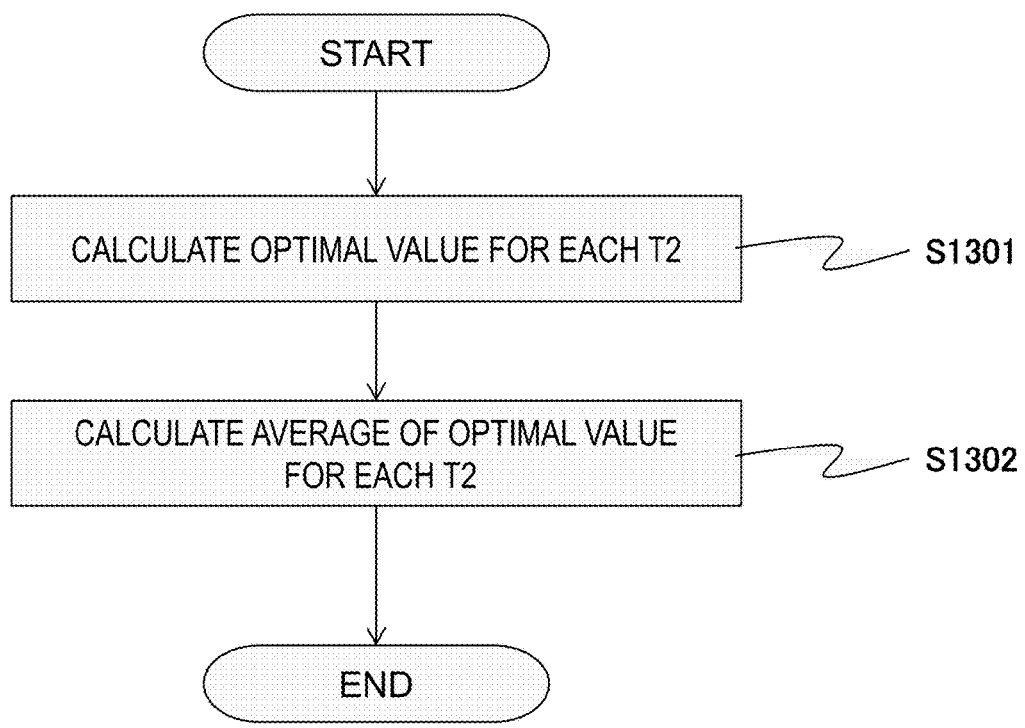
FIG. 14 is a flowchart of the parameter adjustment process when there is a plurality of relaxation times to be considered in the first embodiment.

Alternatively, it may be possible to perform the above-described parameter adjustment process for the respective T2 values and average the obtained optimal values. Thus, FIG. 14 shows the flow of the parameter adjustment process when there is a plurality of relaxation times to be considered. First, for each T2, the optimal value of the adjustment parameter is calculated using a plurality of tissues having the same T2 and different T1 (step S1301). Then, the average of the optimal values obtained for the respective T2 is calculated (step S1302), and the optimal value of the adjustment parameter output as an adjustment result is determined. The method of determining the optimal value for each T2 in step S1301 is the same as the parameter adjustment process described with reference to FIG. 9 or 10 described above.

For example, when two T2 of 50 ms and 100 ms shown in FIGS. 7(a) and 7(b) are taken into consideration, 1.8 seconds is set to the optimal value by taking the average of TR 1.75 seconds when T2 is 50 ms and TR 1.85 seconds when T2 is 100 ms.

Instead of the signal strength, a contrast may be set as an object whose variance is to be minimized. The contrast is calculated by the ratio of the signal strengths Sc(n) of two different T2 values. It is assumed that the T1 values of the tissues, which are the signal strength ratio, are the same. For example, in the examples shown in FIGS. 7(a) and 7(b), assuming that the signal strength of each T1 value when T2 is 50 ms is Sc1(n) and the signal strength of each T1 value when T2 is 100 ms is Sc2(n), the contrast Rc(n) is expressed as Sc1(n)/Sc2(n). The parameter adjusting section 711 searches for a value at which the objective function is minimized with the variance Rcvar of the contrast Rc(n) as an objective function.

Figure 15:
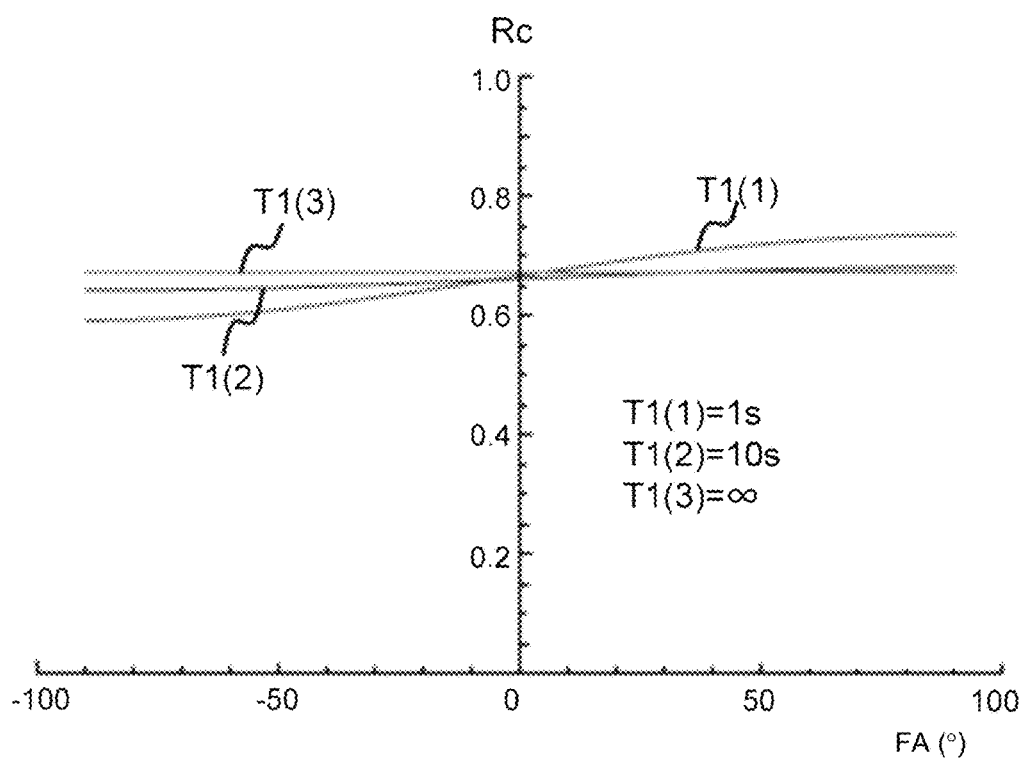
FIG. 15 is a diagram for explaining a specific example of the parameter adjustment when there is a plurality of relaxation times to be considered in the first embodiment.

FIG. 15 shows an adjustment example when the FA of the DE pulse 204 is set as an adjustment parameter and the objective function is the variance Rcvar of the contrast. Here, two T2 are set to 50 ms and 100 ms. In addition, T1 of three tissues having different T1 is set to T1(1)=1 s, T1(2)=10 s, and T1(3)=infinite. Assuming that the signal strength at the k-space center in the tissue having T2 of 50 ms and T1(n) (n=1, 2, 3) is Sc1(n) and the signal strength at the k-space center in the tissue having T2 of 100 ms and T1 of T1(n) is Sc2(n), the objective function Rcvar is the variance of Rc(n)=Sc1(n)/Sc2(n).

The imaging conditions in this case are set to TR=1.8 seconds, ETL=80, and IET=7.3 ms. The FA change shape FAP of the FA of the refocus RF pulse 202 is set to the shape shown in FIG. 4 as in the first embodiment.

In addition, "T1 is infinite" is set by replacing the above Equation (3) with the following Equation (8), and the influence of T1 is neglected in this case. This is based on a virtual state in which there is no T1 attenuation and the longitudinal magnetization returns to the original state immediately before excitation.

$$MT0=1 \quad (8)$$

In the example shown in FIG. 15, it can be seen that the objective function Rcvar is minimized when the FA of the DE pulse 204 is approximately 0°.

As described above, the MRI apparatus 100 of the present embodiment includes the static magnetic field generation unit 120 that generates a static magnetic field, the gradient magnetic field generation unit 130 that applies a gradient magnetic field to the object placed in the static magnetic field, the signal transmission unit 150 that transmits a high-frequency magnetic field pulse to excite the magnetization of the object at a predetermined flip angle, the signal receiving unit 160 that receives an echo signal generated by the object, the control unit 170 that reconstructs an image from the echo signal received by the signal receiving unit and that controls the operations of the gradient magnetic field generation unit 130, the signal transmission unit 150, and the signal receiving unit 160 according to the imaging sequence, the parameter adjusting section 711 that adjusts an imaging parameter to be adjusted, which is set in advance, so as to reduce unnecessary contrast, and the sequence creating section 710 that receives the imaging parameter adjusted by the parameter adjusting section 711 and generates an imaging sequence using the imaging parameter and the pulse sequence.

Here, the pulse sequence is a pulse sequence in which a plurality of refocus high-frequency magnetic field pulses are applied within the repetition time after the application of one excitation high-frequency magnetic field pulse, and the flip angle of at least one of the refocus high-frequency magnetic field pulses is not 180°. Then, the parameter adjusting section 711 adjusts the imaging parameter to be adjusted so as to reduce the T1 contrast.

Thus, according to the present embodiment, it is possible to suppress the mixing of the T1 contrast when capturing the T2-weighted image. In the present embodiment, the mixing of the T1 contrast is suppressed by adjusting the degree of T1 recovery after echo train acquisition. The adjustment is performed according to the length of the TR, application timing of the RF pulse for flip-back/down applied during the recovery period, FA, gradient magnetic field strength, and the like. That is, the T1 contrast is canceled by attenuation and recovery having naturally opposite effects.

If this is explained in simplified Equations, the first-order approximation at T=0 of exp(−T/T1(n)) showing the attenuation is 1−T/T1(n), and the first-order approximation at T=0 of 1−exp (−T/T1(n)) showing the recovery is T/T1(n). Therefore, it is possible to cancel the attenuation and the recovery in the first-order approximation. Since this relationship between the attenuation and the recovery is satisfied for any T1, it is expected to cancel the T1 in a wide range.

According to the present embodiment, the value after the adjustment of the parameter that has been adjusted in order to cancel the influence of T1 is presented to the user. For this reason, the user can grasp the imaging parameter after the adjustment. Therefore, parameter adjustment, such as sacrificing the contrast in order to shorten the imaging time, becomes easier.

For example, in non-VRFA, as the TR increases, the mixing of the T1 contrast is suppressed, and the signal strength increases. For this reason, there has been no need to know the TR that minimizes the mixing of the T1 attenuation. However, from the example described above, in the case of VRFA, it can be seen that the TR minimizing the mixing of T1 attenuation becomes shorter by approximately 2 seconds in the T2-weighted imaging. Thus, if the TR that minimizes the mixing of T1 attenuation can be grasped, it is possible to easily determine whether to shorten the imaging time by reducing the TR or to increase the signal strength by increasing the TR. That is, it is possible to easily determine the trade-offs between the imaging time, contrast, and SNR.

Second Embodiment

Next, a second embodiment to which the present invention is applied will be described. In the first embodiment, when acquiring the T2-weighted image, adjustment parameters are adjusted so as to reduce the influence of T1. On the other hand, in the present embodiment, when acquiring the T1-weighted image, adjustment parameters are adjusted so as to reduce the influence of the T2 contrast.

An MRI apparatus of the present embodiment has basically the same configuration as the MRI apparatus 100 of the first embodiment. The functional configuration of the control unit 170 of the present embodiment is also the same. However, since the images to be acquired are different and the contrasts to be reduced are different as mentioned above, the parameter adjustment process of the parameter adjusting section 711 is different. The pulse sequence to be used and the flow of the imaging process are the same as those in the first embodiment.

The parameter adjusting section 711 of the present embodiment adjusted the imaging parameter set by the user so that the influence of T2 causing unnecessary contrast is reduced. That is, the parameter adjusting section 711 adjusts the imaging parameter to be adjusted so as to reduce the T2 contrast. The adjustment parameter to be adjusted is the same as that in the first embodiment.

Here, the parameter adjustment process of the parameter adjusting section 711 of the present embodiment will be described. The parameter adjusting section 711 of the present embodiment adjusts an adjustment parameter using the signal strengths of echo signals arranged at the k-space center, among echo signals from a plurality of tissues having different combinations of T1 and T2. When T1 is the same, adjustment is performed so that the signal strength difference is reduced even if T2 is different. For example, the difference is reduced by adjusting the adjustment parameter so that the variance of the signal strengths of echo signals arranged at the center of the k space is reduced.

Figure 16:
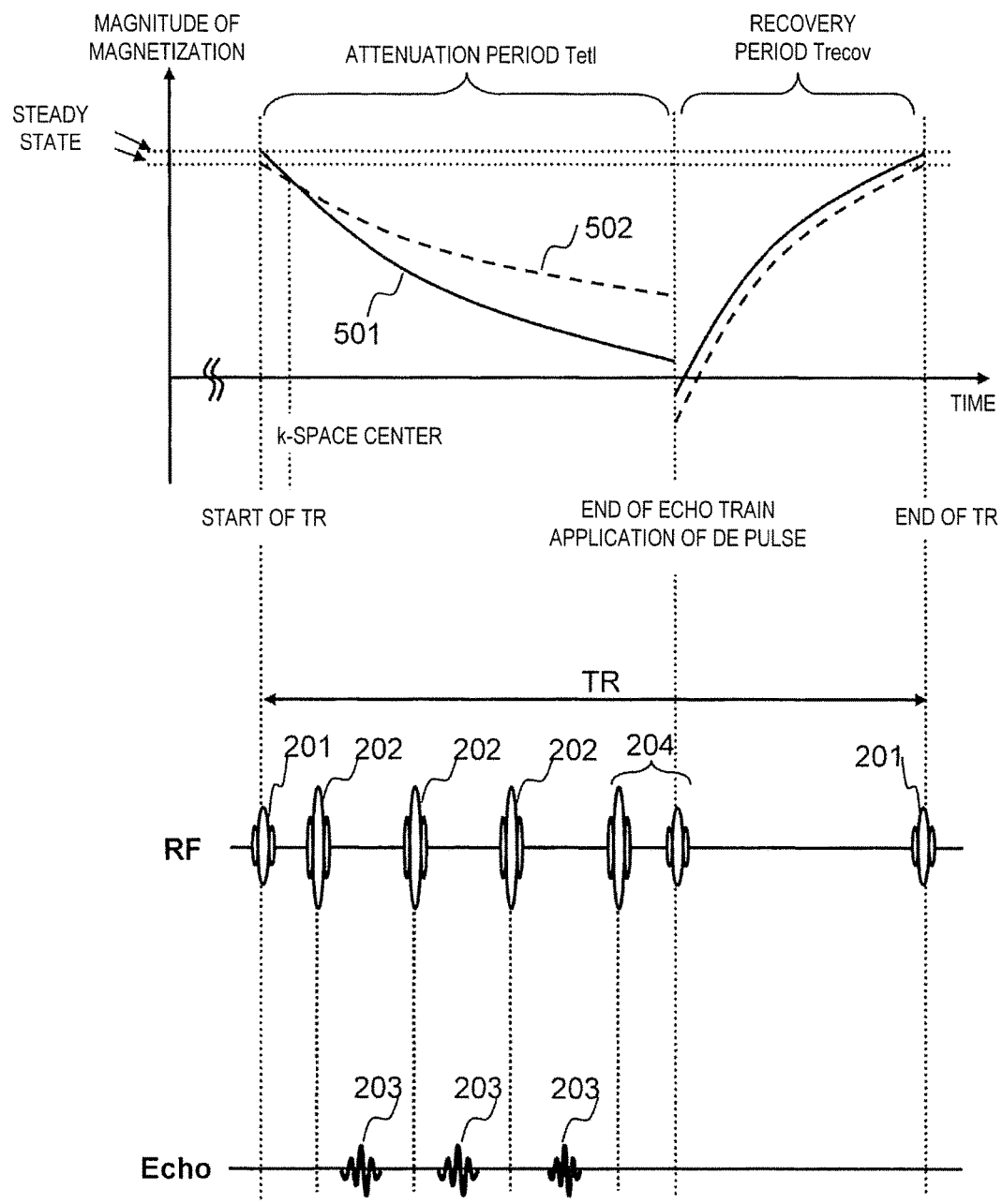
FIG. 16 is a diagram for explaining the adjustment process in a second embodiment.

FIG. 16 shows the relationship between the pulse sequence and changes in the magnitude of magnetization of two tissues C and D having the same longitudinal relaxation time T1 and different transverse relaxation time T2. It is assumed that the transverse relaxation time T2C of the tissue C is shorter than the transverse relaxation time T2D of the tissue D (T2C<T2D). The pulse sequence to be used is assumed to be the VRFA sequence 200 shown in FIG. 3. Also in the present embodiment, the sequence to be used is not limited to the VRFA sequence 200, as in the first embodiment. Any sequence may be used in which the FA of at least one refocus RF pulse 202 is not 180°.

Here, a change (solid line) 501 in the magnitude of magnetization of the tissue C, a change (broken line) 502 in the magnitude of magnetization of the tissue D, the application timings of the excitation RF pulse 201, the refocus RF pulse 202, and the DE pulse 204, and the acquisition timing of the echo signal 203 are shown. Also in this diagram, only the magnitude of magnetization that contributes to the echo signal to be acquired is shown. In addition, a state within 1 TR when the VRFA sequence 200 is sufficiently repeated to realize a steady state is shown.

In the case of using the VRFA sequence 200, as shown in this diagram, when excitation occurs due to the excitation RF pulse 201 after the start of the TR, the magnitudes 501 and 502 of magnetization of both the tissues C and D change until the end of the echo train while refocusing due to the refocus RF pulse 202 occurs. The changes in the magnitudes 501 and 502 of magnetization include T1 attenuation of longitudinal magnetization occurring due to the FA of the refocus RF pulse 202 that is not 180°.

Here, when the DE pulse 204 is applied after the acquisition of the last echo signal of the echo train, magnetization that contributes to the echo signal to be acquired becomes longitudinal magnetization, thereby realizing the T1 recovery until the end of the TR. The recovered longitudinal magnetization contributes to echo signals to be acquired in the next TR. That is, in the next TR, a change is started from the magnitude of magnetization recovered at the end of the last TR. Therefore, the magnitude of magnetization at the end of the TR can be set to the magnitude of magnetization at the start of the next TR, which is optimal in the next TR, by adjusting the degree of recovery of magnetization in the recovery period.

The parameter adjusting section 711 of the present embodiment searches for the adjustment parameter that optimizes the magnitude of the magnetization at the end of the TR. When only the two tissues C and D are taken into consideration, the magnitude of the optimal magnetization at the end of the TR is when the magnitudes (signal strengths) of magnetization of the tissues C and D become approximately equal at a timing, at which the k-space center to determine the contrast is acquired, in the next TR.

More generally, also in the present embodiment, the parameter adjusting section 711 adjusts the adjustment parameters so that the variance Scvar of each signal strength Sc is minimized, as a state in which the signal strengths Sc at the k-space center in the steady state in a plurality of tissues having the same T1 and different T2 are approximately equal. That is, the parameter adjusting section 711 of the present embodiment sets the variance Scvar as an objective function, searches for an adjustment parameter that minimizes the objective function, and determines the adjustment parameter as an optimal value.

A specific method of the above adjustment of the parameter adjusting section 711 of the present embodiment will be described below. Assuming that T2 of each of N (N is an integer of 2 or more) tissues having the same T1 and different T2 is T2(n) (n=1, 2, 3, . . . , N) and the signal strength at the k-space center in the steady state of T2(n) is Sc(n), the objective function is the variance Scvar of "N" Sc(n). The parameter adjusting section 711 of the present embodiment searches for and determines an adjustment parameter that minimizes the objective function Scvar.

Equations required in order to calculate the Sc(n) of the present embodiment are shown below. These equations are basically the same as Equations (1) to (4) in the first embodiment. That is, as in the first embodiment, the magnitude MTend of transverse magnetization at the end of the echo train (immediately before the application of the DE pulse), the magnitude MLde of longitudinal magnetization after the application of the DE pulse 204, the magnitude MT0 of transverse magnetization immediately after excitation, and the signal strength Sc(n) will be described with reference to the following four separate Equations (9) to (12).

$$MTend = MT0 \times Rend(n) \tag{9}$$

$$MLde = MTend \times \sin(-FAde) \tag{10}$$

$$MT0 = 1 - (1 - MLde) \times \exp(-Trecov/T1) \tag{11}$$

$$Sc(n) = MT0 \times Rcent(n) \tag{12}$$

Here, the magnitude of magnetization immediately after excitation after complete recovery is set to 1. FAde is the FA of the DE pulse 204. This is assumed to have the same phase as the excitation pulse (negative at the time of flip-back). Trecov is a time from the application of the DE pulse 204 to the application of the next excitation RF pulse 201 as described above.

Here, Rend(n) that is the ratio of the magnitude of transverse magnetization at the end of the echo train to that at the start of the echo train and Rcent(n) that is the ratio of the magnitude of transverse magnetization at the time of k-space center collection to the magnitude of transverse magnetization at the start of the echo train are values when T2 is T2(n).

These can be calculated from the FA of the refocus RF pulse 202 and T1 and T2 using the Bloch equation. In addition, the timing to collect echo signals arranged at the k space can be arbitrarily changed by echo shift or the like.

In the example described above, the magnitude of longitudinal magnetization MLend at the end of the echo train (immediately before the application of the DE pulse 204) is set to 0 for the sake of simplicity. When the longitudinal magnetization MLend at the end of the echo train is taken into consideration, the longitudinal magnetization component of the MTend is also taken into consideration by adding the longitudinal magnetization version (1-1) of Equation (9) and replacing Equation (10) with Equation (2-1), in the same manner as for Equations (1) to (4). When the DE pulse 204 is not applied, the FA of the DE pulse 204 is set to 0.

The method of searching for the adjustment parameter that minimizes the objective function Scvar is the same as that in the first embodiment. That is, the flow of the parameter adjustment process performed by the parameter adjusting section 711 of the present embodiment is the same as the flow of the parameter adjustment process in the first embodiment described with reference to FIG. 9. For example, when the FA of the DE pulse 204 is set as an adjustment parameter, the parameter adjusting section 711 searches for and determines FAde that minimizes the objective function Scvar.

FIGS. 17(a) and 17(b) show specific examples of adjustment performed by the parameter adjusting section 711 of the present embodiment. FIGS. 17(a) and 17(b) are graphs showing changes in the signal strength Sc at the k-space center in the steady state in four tissues, which have the same T1 and different T2, according to the adjustment parameter. Here, the adjustment parameter is the FA of the DE pulse 204.

Four T2 (T2(1), T2(2), T2(3), T2(4)) are set to T2(1)=80 ms, T2(2) =100 ms, T2(3)=1000 ms, and T2(4)=infinite. FIG. 17(a) is a graph showing a signal strength change in the tissue having T1 of 500 ms, and FIG. 17(b) is a graph showing a signal strength change in the tissue having T1 of 1000 ms. As the imaging conditions, the number of echo trains (ETL) is set to 80, an echo interval (IET) is set to 7.3 ms, and TR is set to 1000 ms. The FA of the refocus RF pulse 202 is changed according to the FA change shape FAP shown in FIG. 4.

As shown in FIG. 17(a), in the case of the tissue having T1 of 500 ms, it can be seen that the FA (optimal value) of the DE pulse 204 minimizing the variance Scvar of the Sc is 40°. In addition, as shown in FIG. 17(b), in the case of the tissue having T1 of 1000 ms, it can be seen that the FA (optimal value) of the DE pulse 204 minimizing the Scvar is 20°.

The present invention is the same as the first embodiment except for the parameter adjustment process described above. That is, the flow of the imaging process performed by the control unit 170 of the present embodiment is the same as that in the first embodiment.

Also in the present embodiment, as in the first embodiment, the length of the recovery period Trecov, an RF waveform applied during the Trecov, and a gradient magnetic field strength applied during the Trecov can be used as adjustment parameters.

For example, when the TR is used as an adjustment parameter, Trecov minimizing the Scvar is determined using Equations (9) to (12) described above.

In addition, when the application timing of the saturation pulse 205 is used as an adjustment parameter, Equation (11) described above is replaced with the following Equations (13) and (14).

$$M\text{sat} = 1 - (1 - ML de) \times \exp(-T\text{recov}1/T1) \quad (13)$$

$$MT0 = 1 - (1 - M\text{sat} \times \cos(FA\text{sat})) \times \exp(-T\text{recov}2/T1) \quad (14)$$

Here, Msat is the magnitude of magnetization immediately before the application of the saturation pulse 205, FAsat is the FA of the saturation pulse 205, Trecov1 is a time from the DE pulse 204 to the application of the saturation pulse 205, and Trecov2 is a time from the saturation pulse 205 to the start of the next echo train.

In addition, the FA of the saturation pulse 205 may be set as an adjustment parameter. In this case, FAsat that minimizes the variance Scvar of Sc(n) with respect to a plurality of n is calculated as an optimal value. It is assumed that the method of searching for the optimal value is the same as that in the above case in which the adjustment parameter is TR.

By setting the saturation pulse 205 as an adjustment parameter, it is possible to reduce the magnetization at a desired timing. Therefore, it is possible to realize the desired T1 recovery regardless of the length of the TR. That is, even if the TR is long, the degree of T1 recovery can be suppressed by delaying the application timing of the saturation pulse 205. Therefore, this is useful for imaging in which it is not possible to designate a short TR, such as synchronous measurement.

In addition, when the above-described adjustment parameters are used in combination, the magnitude of magnetization is calculated using the Bloch equation showing in the above Equation (7), as in the first embodiment.

Also in the present embodiment, the imaging parameter may be adjusted with a simple equation obtained by limiting the Trecov period, the RF waveform, and the gradient magnetic field strength to some extent, instead of solving directly the Bloch equation.

Also in the present embodiment, a limit on the variation range of each adjustment parameter may be set as in the first embodiment. The flow of the parameter adjustment process in this case is the same as that in the first embodiment.

Also in the present embodiment, in the parameter adjustment process, a plurality of T1 may be taken into consideration as in the first embodiment. In this case, as in the first embodiment, the objective function is assumed to be a sum of coefficients of variation of the signal strength Sc with respect to the respective T1 values. When two T1 ($T1_1$ and $T1_2$) are taken into consideration, the above-described parameter adjustment process is performed by using $Sccv_1 + Sccv_2$ as an objective function. $Sccv_1 + Sccv_2$ is a sum of a coefficient of variation $Sccv_1$ of the signal strength at the k-space center obtained by using a plurality of tissues having different T2 when T1 is $T1_1$ and a variance $Sccv_2$ of the signal strength at the k-space center obtained by using a plurality of tissues having different T2 when T1 is $T1_2$. The flow of the process in this case is the same as that of the parameter adjustment process in the first embodiment described with reference to FIG. 9 or 10.

Also in the present embodiment, it may be possible to perform the above-described parameter adjustment process for the respective T1 values and average the obtained optimal values. The flow of the process in this case is the same as the flow of the process in the first embodiment described with reference to FIG. 14.

In addition, as in the first embodiment, it may be possible to use the contrast instead of the signal strength and to calculate the variance as an objective function. That is, the parameter adjusting section 711 may determine a value, which minimizes the variance of the contrast, as an optimal value of the adjustment parameter. The contrast is calculated as a ratio of the signal strengths of two different T1 values.

For example, in the examples shown in FIGS. 17(a) and 17 (b), assuming that the signal strengths of four T2 (n) (n=1, 2, 3, 4) when T1 is 500 ms is Sc1 (n) and the signal strength of four T2 (n) when T1 is 1000 ms is Sc2 (n), the contrast Rc(n) is expressed as Sc1 (n)/Sc2 (n). The parameter adjusting section 711 sets the Rc(n) as an objective function, and determines a value minimizing the variance Rcvar as an optimal value of the adjustment parameter.

Figure 18:
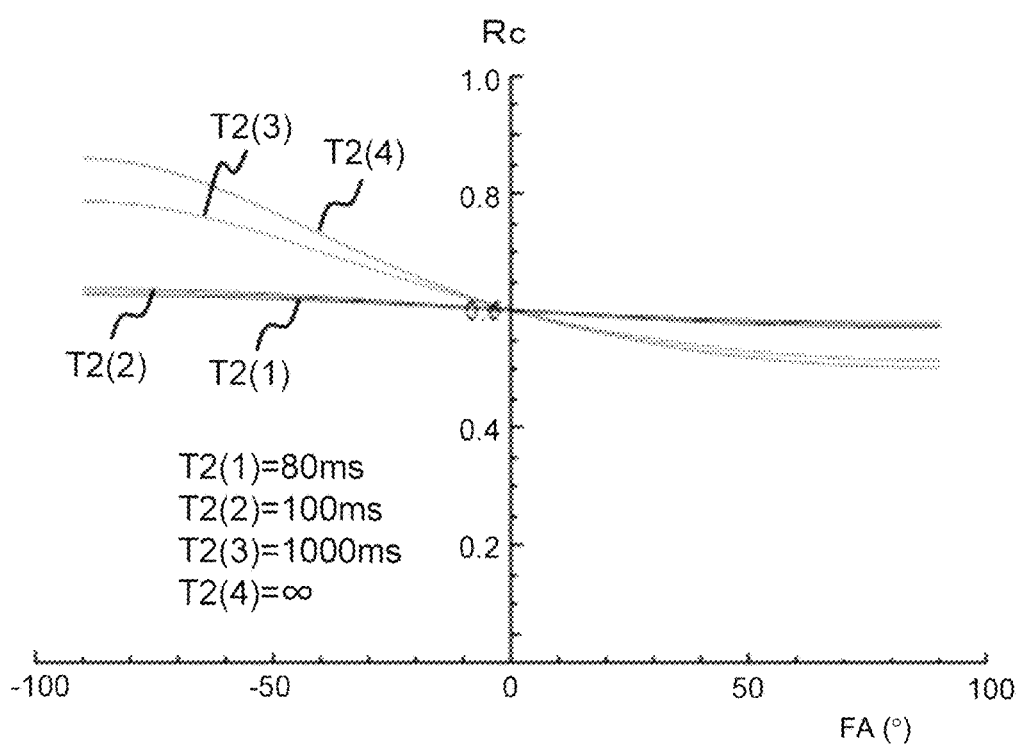
FIG. 18 is a diagram for explaining the adjustment process when the adjustment parameter is the flip angle of a DE pulse in the second embodiment.

FIG. 18 shows a graph of the contrast Rc for each T2 (n) when the FA of the DE pulse 204 is set as an adjustment parameter. As shown in this diagram, in this case, 0° is obtained as an optimal value. As can be seen from FIGS. 17(a) and 17 (b), even if T1 is the same, the signal strength changes greatly if T2 is different. That is, the T2 contrast is included in the T1-weighted image. Therefore, when the T2 for imaging is in a narrow range, it is possible to apply a process in which the contrast is used.

As described above, the MRI apparatus 100 of the present embodiment includes the static magnetic field generation unit 120 that generates a static magnetic field, the gradient magnetic field generation unit 130 that applies a gradient magnetic field to the object placed in the static magnetic field, the signal transmission unit 150 that transmits a high-frequency magnetic field pulse to excite the magnetization of the object at a predetermined flip angle, the signal receiving unit 160 that receives an echo signal generated by the object, the control unit 170 that reconstructs an image from the echo signal received by the signal receiving unit and that controls the operations of the gradient magnetic field generation unit 130, the signal transmission unit 150, and the signal receiving unit 160 according to the imaging sequence, the parameter adjusting section 711 that adjusts an imaging parameter to be adjusted, which is set in advance, so as to reduce unnecessary contrast, and the sequence creating section 710 that receives the imaging parameter adjusted by the parameter adjusting section 711 and generates an imaging sequence using the imaging parameter and the pulse sequence. Here, the pulse sequence is a pulse sequence in which a plurality of refocus high-frequency magnetic field pulses are applied within the repetition time after the application of one excitation high-frequency magnetic field pulse, and the flip angle of at least one of the refocus high-frequency magnetic field pulses is not 180°. Then, the parameter adjusting section 711 adjusts the imaging parameter to be adjusted so as to reduce the T2 contrast.

Thus, according to the present embodiment, it is possible to suppress the mixing of the T2 contrast when capturing the T1-weighted image. It is known that flip-down in the DE pulse 204 is sufficient to just increase the T1 contrast. However, the T2 contrast cannot be canceled with the flip-down. Therefore, it can be seen that, when creating an image of only the T1 contrast by canceling the T2 contrast, it is better to use the FA according to the conditions rather than a complete flip-down.

According to the present embodiment, the value after the adjustment of the parameter that has been adjusted in order to cancel the influence of T2 is presented to the user. For this reason, the user can grasp the imaging parameter after the adjustment. Therefore, parameter adjustment, such as sacrificing the contrast in order to shorten the imaging time, becomes easier.

In each of the embodiments described above, the optimal value of the adjustment parameter is determined by performing the parameter adjustment process whenever the imaging parameter is set. However, the present invention is not limited thereto. For example, the optimal value of the adjustment parameter may be calculated in advance for each of the imaging conditions, and be stored in the storage device 172 or the like. The optimal value is calculated according to the FA change shape FAP, imaging target contrast, and the like, for example. In this case, whenever the imaging parameter is set, the optimal value that is stored so as to match the set imaging parameter is acquired.

Figure 19:
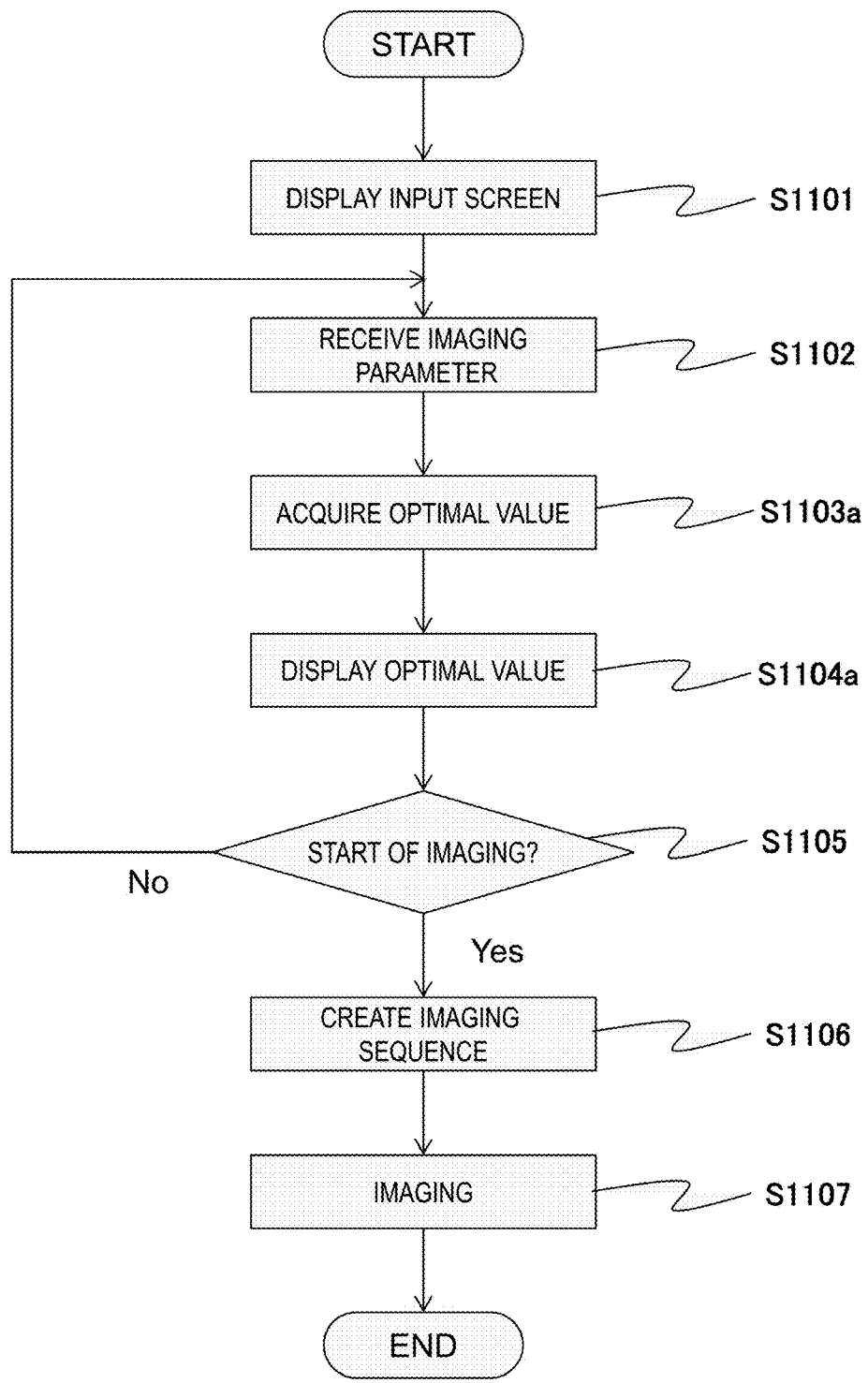
FIG. 19 is a flowchart of the imaging process of a modification example of the embodiment of the present invention.

FIG. 19 shows the process flow of the imaging process when calculating the optimal value in advance. This process is basically the same as the imaging process described with reference to FIG. 8. However, when the imaging conditions are received in step S1102, the optimal value that is stored so as to match the imaging conditions is acquired (step S1103a), and the acquired optimal value will be displayed on the imaging parameter input screen 400 (step S1104a).

Here, a method of increasing the TR without changing the contrast will be described. This method may be applied after adjusting the adjustment parameter with the method of each embodiment described above.

Figure 20:
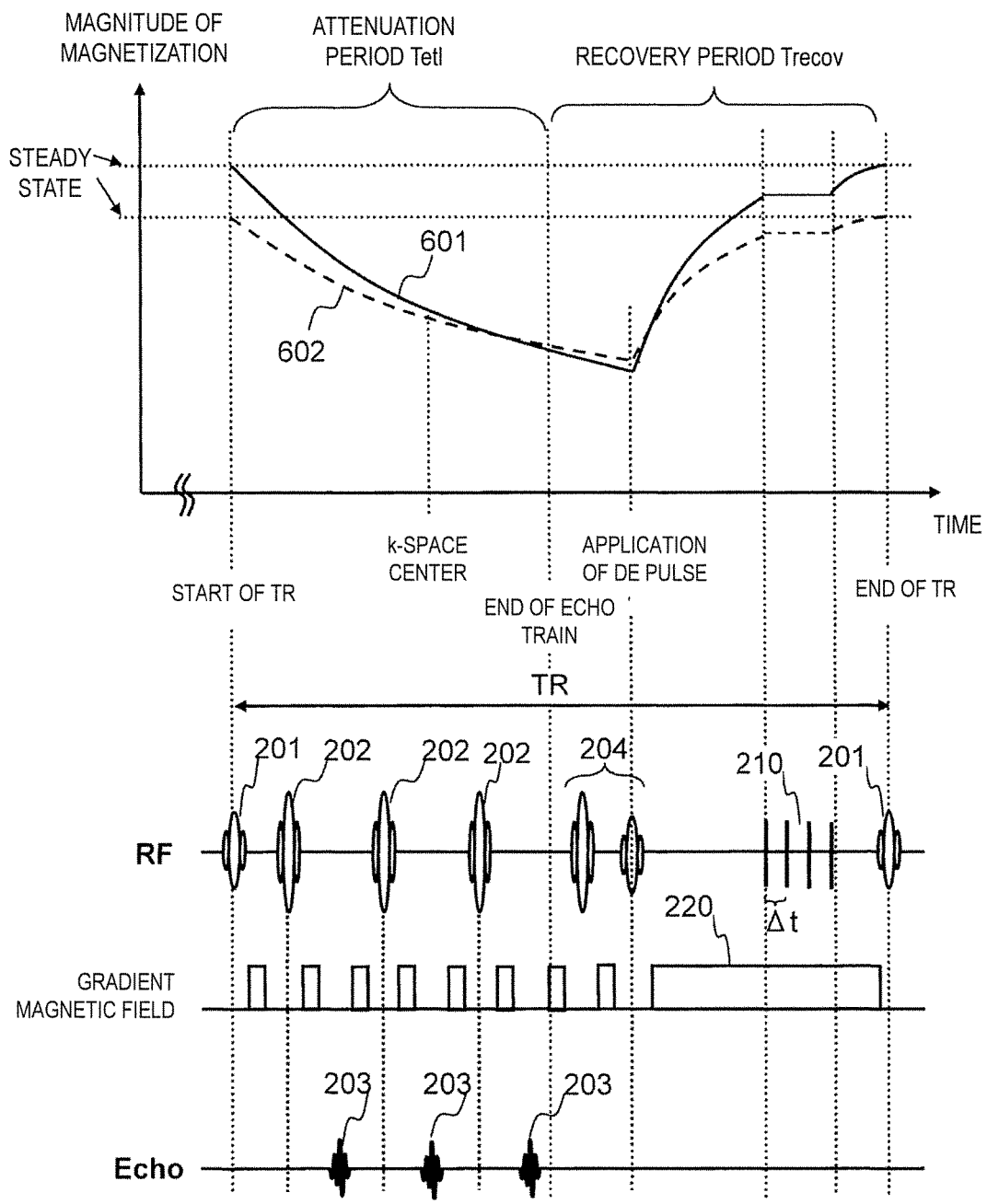
FIG. 20 is a diagram for explaining the adjustment process of the modification example of the embodiment of the present invention.

FIG. 20 is a diagram for explaining this method. Here, as an example, changes 601 and 602 in the magnitude of magnetization of two tissues A and B having the same conditions as in FIG. 6, application timings of RF pulses 201, 202, and 204, application timing of the gradient magnetic field, and acquisition timing of the echo signal 203 are shown.

As shown by the one-dot chain line 600 in FIG. 6, even if T1 is different, there is a timing at which the rates of change in the magnitude of magnetization become close to each other. Here, as shown in FIG. 20, an RF pulse 210 to set the appropriate FA is repeatedly applied at this timing. The magnitude of magnetization at this timing is maintained by repeatedly applying the RF pulse 210.

Although the phase of the RF pulse 210 may be used for spoiling, an example of using a gradient magnetic field 220 is shown in FIG. 20. The gradient magnetic field 220 may be switched so as not to be applied during the application of the RF pulse 210. In addition, when the application time of the RF pulse 210 is so short that the RF pulse 210 is not substantially sliced, the switching is not required.

The FA of the RF pulse 210 applied is determined by the following Equation (15).

$$1-\cos(FA_{SS}) = \Delta m \tag{15}$$

Here, FAss is the FA of the RF pulse 210 that is continuously applied, and $\Delta m$ is the ratio of the magnitude of magnetization that changes during the application interval $\Delta t$ of the RF pulse 210. For example, when the magnetization of magnitude M1 is changed to the magnetization of magnitude M2, $\Delta m = (M2-M1)/M1$. Alternatively, $\Delta m = dM/dt/M1 \times \Delta t$ may be set using the instantaneous rate of change.

By using this method, when starting the echo train after irregular trigger, such as synchronous measurement, in a state in which the magnetization has recovered to some extent, it is possible to wait for a trigger while maintaining the state. Therefore, it becomes easy to control the contrast.

In each of the embodiments described above, the variance or the coefficient of variation (variance/average) of the signal strength Sc at the k-space center in the steady state is used as an objective function. However, the objective function is not limited thereto. For example, a distribution range (difference between the maximum value and the minimum value) may also be used. As described above, it is possible to use any objective function for which the adjustment process described in the first embodiment can be realized, such as adjustment to reduce the difference between the signal strengths of echo signals arranged at the k-space center, for tissues having the same relaxation time (for example, T2) to cause intended contrast and different relaxation times (for example, T1) to cause unnecessary contrast, among the echo signals of a plurality of tissues having different relaxation times.

REFERENCE SIGNS LIST

100: MRI apparatus
101: object
120: static magnetic field generation unit
130: gradient magnetic field generation unit
131: gradient magnetic field coil
132: gradient magnetic field power supply
140: sequencer
150: signal transmission unit
151: transmission coil
152: high frequency oscillator
153: modulator
154: high frequency amplifier
160: signal receiving unit
161: receiving coil
162: signal amplifier
163: quadrature phase detector
164: A/D converter
170: control unit
171: CPU
172: storage device
173: display device
174: input device
200: FSE pulse sequence (VRFA sequence)
201: excitation RF pulse
202: refocus RF pulse
203: echo signal
204: DE pulse
205: saturation pulse
206: RF pulse waveform
207: gradient magnetic field
210: RF pulse
200a: sequence within TR
220: gradient magnetic field
301: change in magnitude of magnetization of tissue A
302: change in magnitude of magnetization of tissue B
400: imaging parameter input screen
401: adjustment parameter input region
402: adjustment parameter display region
403: contrast adjustment setting region
404: reflection button
410: imaging parameter setting region
420: determination button
501: change in magnitude of magnetization of tissue C
502: change in magnitude of magnetization of tissue D
600: timing at which rates of change in magnitude of magnetization become close to each other
601: change in magnitude of magnetization of tissue A
602: change in magnitude of magnetization of tissue B
710: sequence creating section
711: parameter adjusting section
720: imaging section

The invention claimed is:

1. A magnetic resonance imaging apparatus, comprising:
a static magnetic field generation unit that generates a static magnetic field;
a gradient magnetic field generation unit that applies a gradient magnetic field to an object placed in the static magnetic field;
a signal transmission unit that transmits a high-frequency magnetic field pulse to excite magnetization of the object at a predetermined flip angle;
a signal receiving unit that receives an echo signal generated by the object;
a parameter adjusting unit that adjusts an imaging parameter to be adjusted, which is set in advance, so as to reduce unnecessary contrast;
a sequence creating unit that generates an imaging sequence using the imaging parameter adjusted by the parameter adjusting unit and a pulse sequence for applying an excitation high-frequency magnetic field pulse and a plurality of refocus high-frequency magnetic field pulses, of which one or more flip angles are not 180°, within a repetition time; and
a control unit that reconstructs a magnetic resonance image from an echo signal received by the signal receiving unit and that controls operations of the gradient magnetic field generation unit, the signal transmission unit, and the signal receiving unit according to the imaging sequence,
wherein the pulse sequence generated by the sequence creating unit is configured to cause the echo signal to change in longitudinal relaxation time and transverse relaxation time during application of the plurality of refocus high-frequency magnetic field pulses in the pulse sequence,
the imaging parameter to be adjusted includes a parameter that controls at least one of the high-frequency magnetic field pulse and the gradient magnetic field which is applied during a recovery period between application of a last refocus high-frequency magnetic field pulse and application of a next excitation high-frequency magnetic field pulse, and
the parameter adjusting unit (i) adjusts the imaging parameter in order to reduce unnecessary contrast differences between echo signals arranged at k-space center for tissues having same longitudinal relaxation time and different transverse relaxation time to make a magnetic resonance image having a contrast weighted with longitudinal relaxation time or (ii) adjusts the imaging parameter in order to reduce unnecessary contrast differences between echo signals arranged at k-space center for tissues having different longitudinal relaxation time and same transverse relaxation time to make a magnetic resonance image having a contrast weighted with transverse relaxation time.

2. The magnetic resonance imaging apparatus according to claim 1,
wherein the parameter adjusting unit adjusts the imaging parameter to be adjusted so as to reduce T1 contrast or T2 contrast.

3. The magnetic resonance imaging apparatus according to claim 1,
wherein the imaging parameter to be adjusted is a repetition time.

4. The magnetic resonance imaging apparatus according to claim 1, wherein when the imaging parameter to be adjusted includes an application parameter of the high-frequency magnetic field pulse, the application parameter is a flip angle or an application timing of the high-frequency magnetic field pulse.

5. The magnetic resonance imaging apparatus according to claim 4,
wherein the high-frequency magnetic field pulse is a DE pulse or a saturation pulse.

6. The magnetic resonance imaging apparatus according to claim 1,
wherein the adjustable range of the imaging parameter to be adjusted is limited to a variation range set in advance.

7. The magnetic resonance imaging apparatus according to claim 1,
wherein the parameter adjusting unit adjusts the imaging parameter to be adjusted so that a variance of signal strengths of echo signals arranged at k-space center, among echo signals from a plurality of tissues having the same first relaxation time to cause intended contrast and different second relaxation times to cause the unnecessary contrast, is minimized.

8. The magnetic resonance imaging apparatus according to claim 1,
wherein the parameter adjusting unit calculates a ratio of signal strengths of echo signals arranged at k-space, between two tissues having the same second relaxation time to cause the unnecessary contrast and different first relaxation times to cause intended contrast, for a plurality of the different second relaxation times, and adjusts the imaging parameter to be adjusted so as to minimize a variance of the calculation results.

9. The magnetic resonance imaging apparatus according to claim 7,
wherein the parameter adjusting unit calculates a plurality of variances of the signal strengths of the echo signals arranged at the k-space center while changing the first relaxation time, and adjusts the imaging parameter to be adjusted so as to minimize a sum of the calculation results.

10. The magnetic resonance imaging apparatus according to claim 7,
wherein the parameter adjusting unit calculates a plurality of the imaging parameters to be adjusted so as to minimize a variance of the signal strengths of the echo signals arranged at the k-space center while changing the first relaxation time, and calculates an average value of the calculation results as an adjustment result.

11. The magnetic resonance imaging apparatus according to claim 1,
wherein the parameter adjusting unit generates an imaging parameter input screen to receive the imaging parameter, and
the imaging parameter input screen includes at least one of an adjustment parameter display region where a value after the adjustment of the imaging parameter to be adjusted is displayed, a reflection button to receive an instruction to reflect the value after the adjustment of the imaging parameter to be adjusted on the imaging parameter, and a contrast adjustment setting region to receive a designation of intended contrast.

12. A method for reducing unnecessary contrast in a magnetic resonance imaging apparatus including a static magnetic field generation unit that generates a static magnetic field, a gradient magnetic field generation unit that applies a gradient magnetic field to an object placed in the static magnetic field, a signal transmission unit that transmits a high-frequency magnetic field pulse to excite magnetization of the object at a predetermined flip angle, a signal receiving unit that receives an echo signal generated by the object, and a control unit that controls operations of the gradient magnetic field generation unit, the signal transmission unit, and the signal receiving unit, the method comprising;
a parameter adjusting step of causing the control unit to adjust an imaging parameter to be adjusted, which is set in advance, so as to reduce unnecessary contrast;
a sequence creating step of causing the control unit to generate an imaging sequence using the adjusted imaging parameter and a pulse sequence for applying an excitation high-frequency magnetic field pulse and a plurality of refocus high-frequency magnetic field pulses, of which one or more flip angles are not 180°, within a repetition time; and
a reconstructing step of causing the control unit to reconstruct a magnetic resonance image from an echo signal received by the signal receiving unit by executing the imaging sequence,
wherein the pulse sequence generated in the sequence creating step is configured to cause the echo signal to change in longitudinal relaxation time and transverse relaxation time during application of the plurality of refocus high-frequency magnetic field pulses in the pulse sequence,
the imaging parameter to be adjusted includes a parameter that controls at least one of the high-frequency magnetic field pulse and the gradient magnetic field which is applied during a recovery period between application of a last refocus high-frequency magnetic field pulse and application of a next excitation high-frequency magnetic field pulse, and
the parameter adjusting step (i) adjusts the imaging parameter in order to reduce unnecessary contrast differences between echo signals arranged at k-space center for tissues having same longitudinal relaxation time and different transverse relaxation time to make a magnetic resonance image having a contrast weighted with longitudinal relaxation time or (ii) adjusts the imaging parameter in order to reduce unnecessary contrast differences between echo signals arranged at k-space center for tissues having different longitudinal relaxation time and same transverse relaxation time to make a magnetic resonance image having a contrast weighted with transverse relaxation time.

13. The method according to claim 12, wherein the parameter adjusting unit adjusts the imaging parameter to be adjusted so as to reduce T1 contrast or T2 contrast.

14. The method according to claim 12,
wherein the imaging parameter to be adjusted is a repetition time.

15. The method according to claim 12, wherein when the imaging parameter to be adjusted includes an application parameter of the high-frequency magnetic field pulse, the application parameter is a flip angle or an application timing of the high-frequency magnetic field pulse.

16. The method according to claim 12,
wherein the parameter adjusting unit adjusts the imaging parameter to be adjusted so that a variance of signal strengths of echo signals arranged at k-space center, among echo signals from a plurality of tissues having the same first relaxation time to cause intended contrast and different second relaxation times to cause the unnecessary contrast, is minimized.

17. The method according to claim 12, wherein the parameter adjusting unit calculates a ratio of signal strengths of echo signals arranged at k-space, between two tissues having the same second relaxation time to cause the unnecessary contrast and different first relaxation times to cause intended contrast, for a plurality of the different second relaxation times, and adjusts the imaging parameter to be adjusted so as to minimize a variance of the calculation results.

18. The method according to claim 12,
wherein the parameter adjusting unit calculates a plurality of variances of signal strengths of echo signals arranged at the k-space center, among echo signals from a plurality of tissues having the same first relaxation time to cause intended contrast and different second relaxation times to cause the unnecessary contrast, while changing the first relaxation time, and adjusts the imaging parameter to be adjusted so as to minimize a sum of the calculation results.

19. The method according to claim 12,
wherein the parameter adjusting unit calculates a plurality of the imaging parameters to be adjusted so as to minimize a variance of signal strengths of echo signals arranged at the k-space center, among echo signals from a plurality of tissues having the same first relaxation time to cause intended contrast and different second relaxation times to cause the unnecessary contrast, while changing the first relaxation time, and calculates an average value of the calculation results as an adjustment result.

* * * * *